(12) United States Patent
Hatano et al.

(10) Patent No.: US 10,324,142 B2
(45) Date of Patent: Jun. 18, 2019

(54) DIAMOND CRYSTAL, DIAMOND DEVICES, MAGNETIC SENSOR, MAGNETIC SENSOR SYSTEM, AND METHOD FOR MANUFACTURING SENSOR ARRAY

(71) Applicants: JAPAN SCIENCE AND TECHNOLOGY AGENCY, Kawaguchi-shi (JP); NATIONAL INSTITUTE OF ADVANCED INDUSTRIAL SCIENCE AND TECHNOLOGY, Chiyoda-ku (JP)

(72) Inventors: Mutsuko Hatano, Tokyo (JP); Takayuki Iwasaki, Tokyo (JP); Norikazu Mizuochi, Osaka (JP); Toshiharu Makino, Ibaraki (JP); Hiromitsu Kato, Ibaraki (JP); Satoshi Yamasaki, Ibaraki (JP)

(73) Assignees: JAPAN SCIENCE AND TECHNOLOGY AGENCY, Kawaguchi-shi (JP); NATIONAL INSTITUTE OF ADVANCED INDUSTRIAL SCIENCE AND TECHNOLOGY, Chiyoda-ku (JP)

( * ) Notice: Subject to any disclaimer, the term of this patent is extended or adjusted under 35 U.S.C. 154(b) by 140 days.

(21) Appl. No.: 15/112,351

(22) PCT Filed: Jan. 19, 2015

(86) PCT No.: PCT/JP2015/000193
§ 371 (c)(1),
(2) Date: Jul. 18, 2016

(87) PCT Pub. No.: WO2015/107907
PCT Pub. Date: Jul. 23, 2015

(65) Prior Publication Data
US 2016/0334474 A1    Nov. 17, 2016

(30) Foreign Application Priority Data

Jan. 20, 2014 (JP) ................................ 2014-008127

(51) Int. Cl.
*G01R 33/032* (2006.01)
*C30B 29/04* (2006.01)
(Continued)

(52) U.S. Cl.
CPC .............. *G01R 33/032* (2013.01); *C30B 25/02* (2013.01); *C30B 25/20* (2013.01); *C30B 29/04* (2013.01);
(Continued)

(58) Field of Classification Search
CPC .................................................... G01R 33/032
(Continued)

(56) References Cited

U.S. PATENT DOCUMENTS 9,551,763 B1 * 1/2017 Hahn ................. G01R 33/0017
9,817,081 B2 * 11/2017 Hahn .................. G01R 33/032
(Continued)

FOREIGN PATENT DOCUMENTS

JP    2011-529018 A    12/2011
JP    2012-110489 A    6/2012
(Continued)

OTHER PUBLICATIONS

D. Le Sage, et al., "Optical magnetic imaging of living cells", Nature, vol. 496, Total 6 Pages, (Apr. 25, 2013).
(Continued)

*Primary Examiner* — Reena Aurora
(74) *Attorney, Agent, or Firm* — Oblon, McClelland, Maier & Neustadt, L.L.P.

(57) ABSTRACT

A diamond crystal according to the present invention has an NV region containing a complex (NV center) of nitrogen
(Continued)

substituted with a carbon atom and a vacancy located adjacent to the nitrogen, on a surface or in the vicinity of the surface, wherein the NV region has a donor concentration equal to or higher than the concentration of the NV centers, or a crystal of the NV region is a {111} face or a face having an off-angle that is ±10 degrees or less against the {111} face, and a principal axis of the NV center is a <111> axis that is perpendicular to the {111} face. Such a diamond crystal enables almost 100% of the NV center to be a state ($NV^-$) of having a negative electric charge, and spin states of the $NV^-$ centers to be aligned in one direction.

15 Claims, 18 Drawing Sheets

(51) Int. Cl.

| | | |
|---|---|---|
| G01R 33/00 | (2006.01) | |
| G01R 33/12 | (2006.01) | |
| C30B 25/02 | (2006.01) | |
| C30B 25/20 | (2006.01) | |
| G01N 24/10 | (2006.01) | |
| G01R 33/24 | (2006.01) | |
| G01R 33/32 | (2006.01) | |

(52) U.S. Cl.
CPC ......... *G01N 24/10* (2013.01); *G01R 33/0052* (2013.01); *G01R 33/0094* (2013.01); *G01R 33/1284* (2013.01); *G01R 33/24* (2013.01); *G01R 33/323* (2013.01)

(58) Field of Classification Search
USPC ....................................................... 324/244.1
See application file for complete search history.

(56) References Cited

U.S. PATENT DOCUMENTS

| 9,910,104 B2 * | 3/2018 | Boesch ................ G01R 33/032 |
|---|---|---|
| 2010/0308813 A1 | 12/2010 | Lukin et al. |
| 2010/0315079 A1 | 12/2010 | Lukin et al. |
| 2011/0315988 A1 | 12/2011 | Yu et al. |

| 2012/0051996 A1 | 3/2012 | Scarsbrook et al. |
|---|---|---|
| 2014/0037932 A1 | 2/2014 | Twitchen et al. |
| 2015/0303333 A1 | 10/2015 | Yu et al. |

FOREIGN PATENT DOCUMENTS

| JP | 2012-121747 A | 6/2012 |
|---|---|---|
| JP | 2012-121748 A | 6/2012 |
| WO | 2012/152617 A1 | 11/2012 |

OTHER PUBLICATIONS

J. R. Maze, et al., "Nanoscale magnetic sensing with an individual electronic spin in diamond", Nature, Total 5 Pages, vol. 455, (Oct. 2, 2008).

V. M. Acosta, et al., "Diamonds with a high density of nitrogen-vacancy centers for magnetometry applications", Physical Review B, vol. 80, pp. 115202-1-115202-15, (2009).

Sungkun Hong, et al., "Nanoscale magnetometry with NV centers in diamond", M R S Bulletin, vol. 38, pp. 155-161, (Feb. 2013).

Y. Doi, et al., "Charge Manipulation of a Single NV Center by Current Injection into a Pin Diamond Semiconductor", NDF-DIA. SYMP, vol. 26, Total 7 Pages, (2012), (with English Translation).

A Tallaire, et al., "High quality thick CVD diamond films homoepitaxially grown on (111)-oriented substrates", Diamond & Related Materials, vol. 41, pp. 34-40, (2014).

International Search Report dated Apr. 21, 2015 in PCT/JP15/000193 Filed Jan. 19, 2015.

Extended European Search Report dated Nov. 9, 2017 in Patent Application No. 15737807.6, citing documents AA-AD and AV-AY therein, 10 pages.

Norikazu Mizuochi, "Electrically driven single photon source at room temperature by using single NV center in diamond", The Optical Society of America, XP032603313, 2013, 2 Pages.

Satoshi Koizumi, et al. "Ultraviolet Emission from a Diamond pn Junction", Science, American Association for the Advancement of Science, vol. 292. No. 5523, XP002520859, 2001, pp. 1899-1901.

David M. Toyli, et al. "Chip-scale nanofabrication of single spins and spin arrays in diamond", Nano Letters, vol. 10, No. 8, XP055413827, 2010, 15 pages.

Hiromitsu Kato, et al. "Tunable light emission from nitrogen-vacancy centers in single crystal diamond PIN diodes", Applied Physics Letters, vol. 102, No. 15, XP012171908, 2013, pp. 151101-1-151101-4.

* cited by examiner

FIG.1    Prior Art

FIG.4
(A)
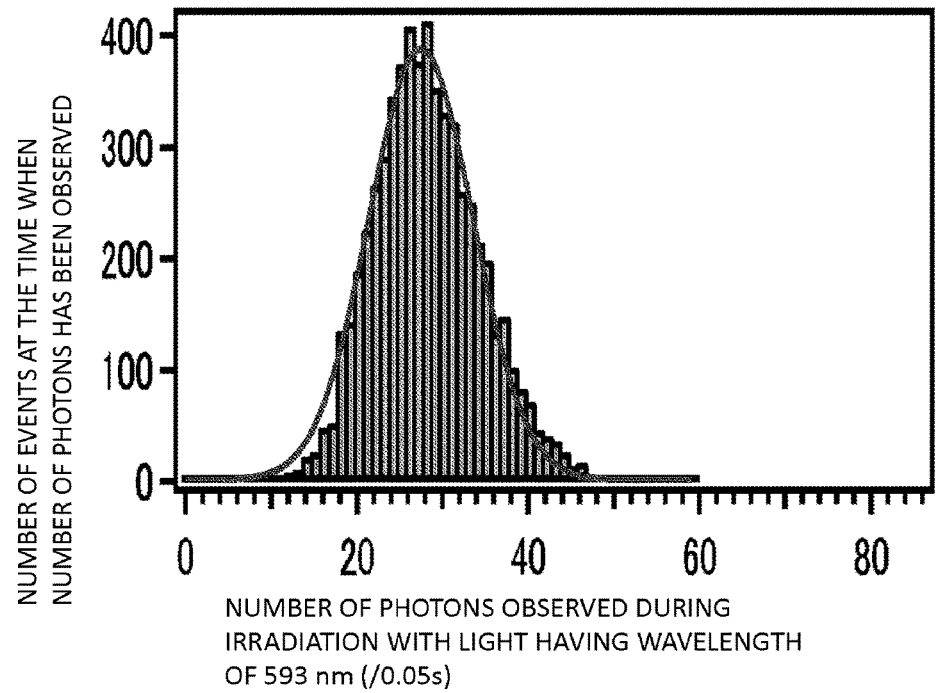
NUMBER OF PHOTONS OBSERVED DURING IRRADIATION WITH LIGHT HAVING WAVELENGTH OF 593 nm (/0.05s)
(B)
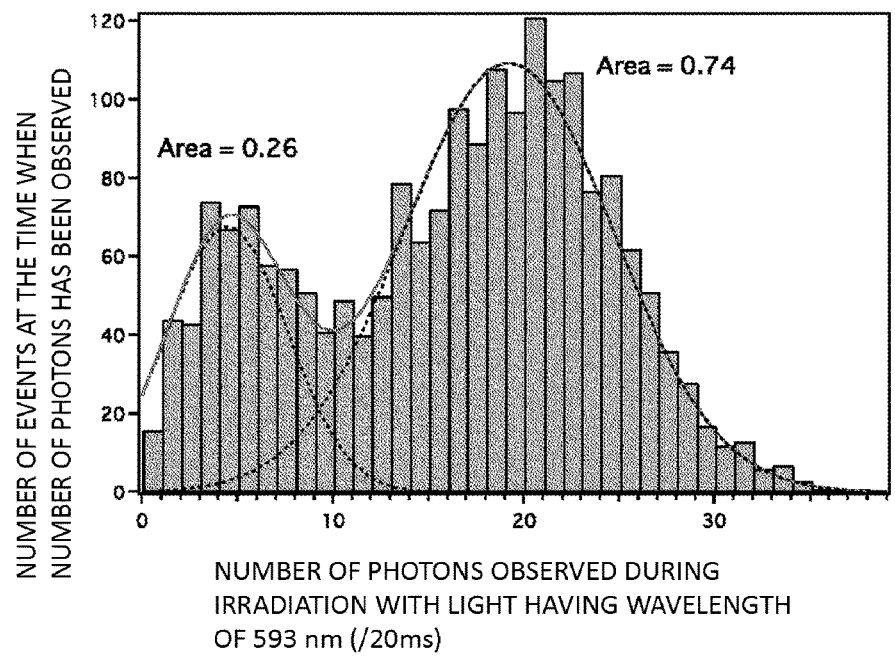
NUMBER OF PHOTONS OBSERVED DURING IRRADIATION WITH LIGHT HAVING WAVELENGTH OF 593 nm (/20ms)

(A)  (B)

FIG.6
(A)
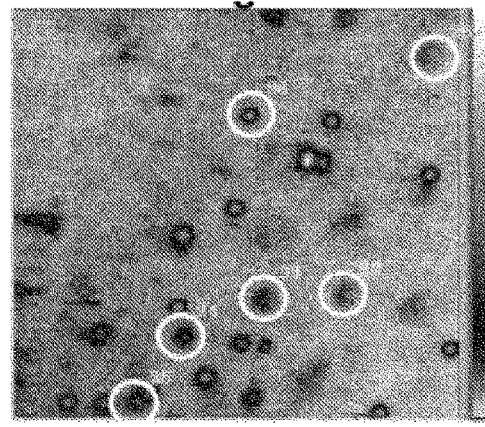
(B)
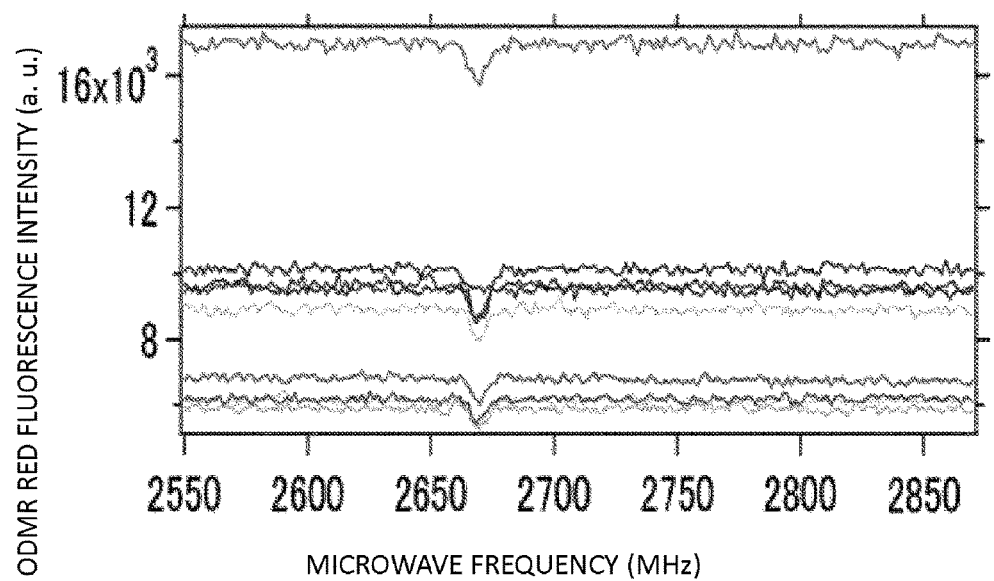

FIG.9
(A)
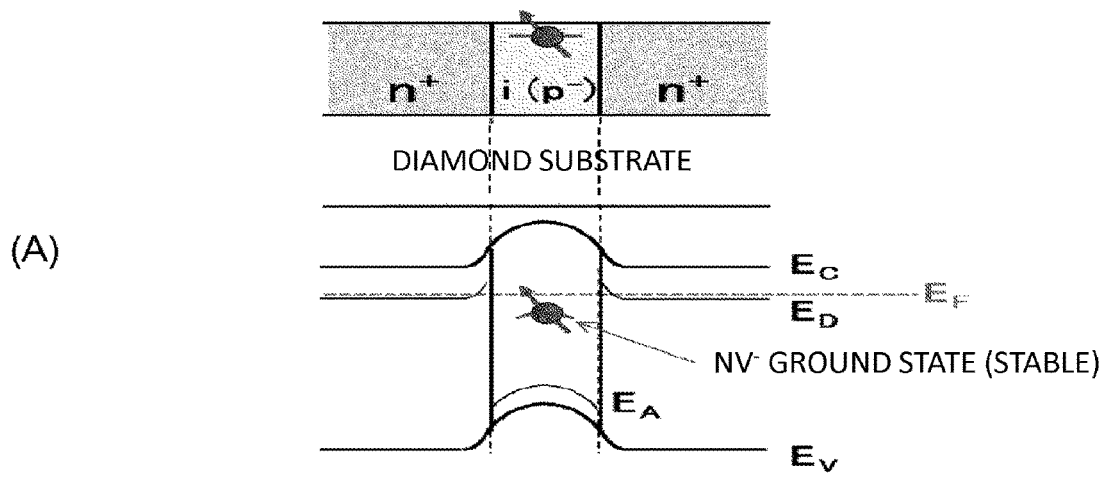
(a)
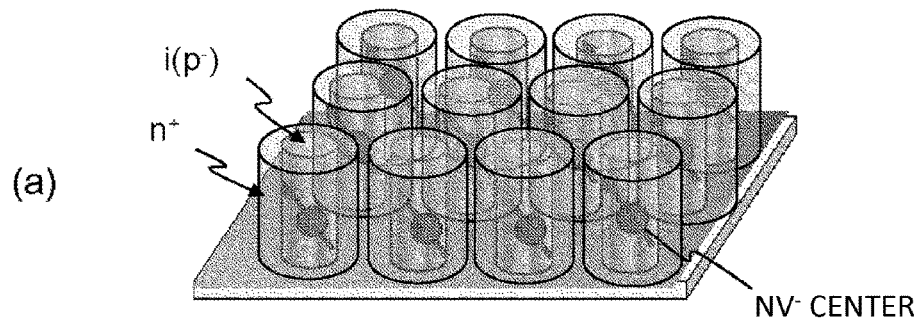
(B)
(b)
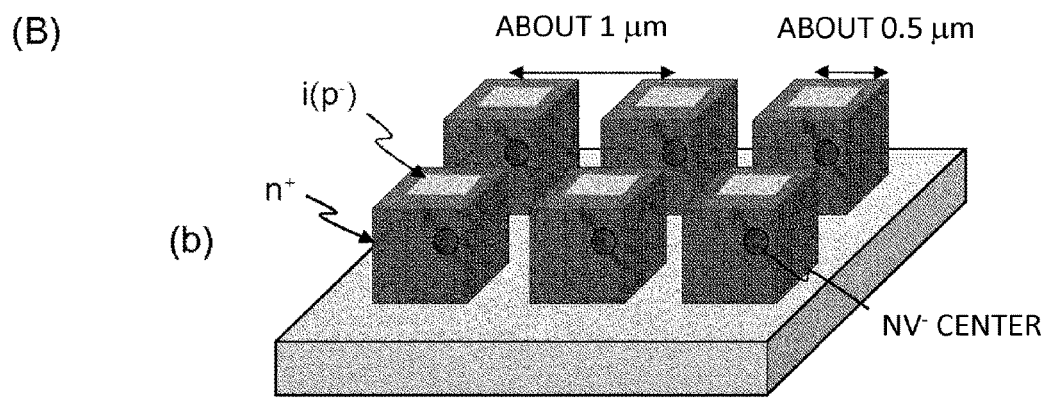

FIG.10
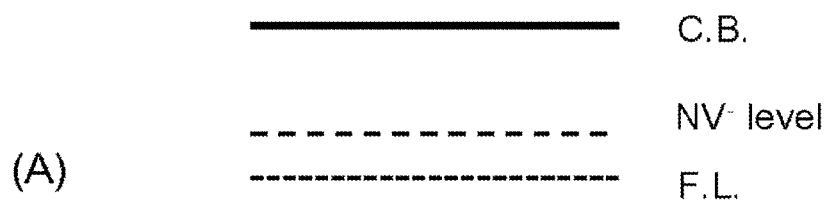
(A)
FIRST REGION
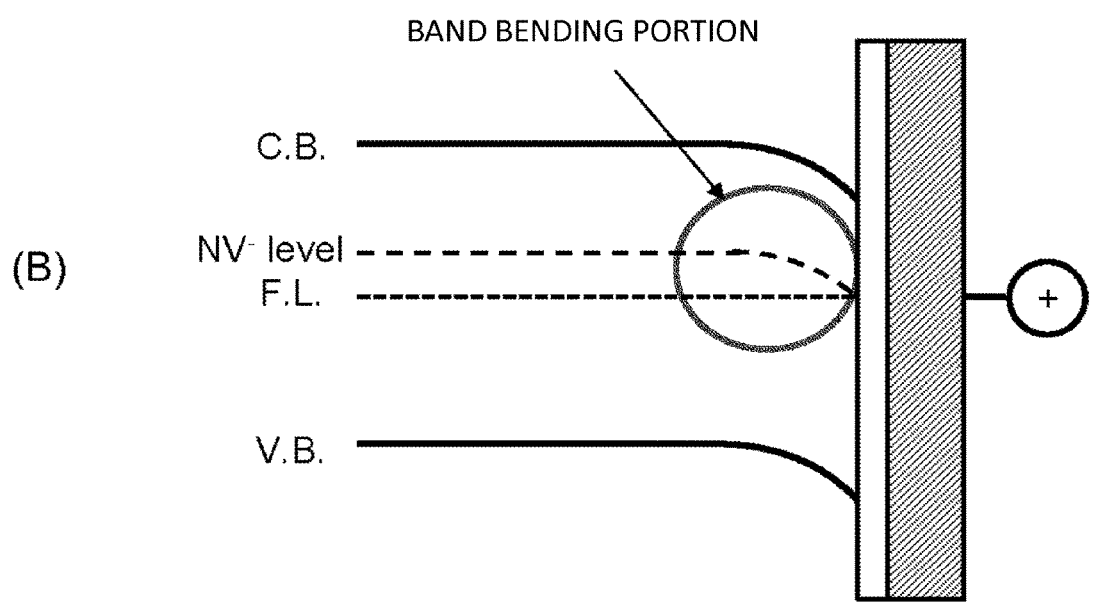
(B)
FIRST REGION   INSULATING FILM   ELECTRODE

DIAMOND CRYSTAL, DIAMOND DEVICES, MAGNETIC SENSOR, MAGNETIC SENSOR SYSTEM, AND METHOD FOR MANUFACTURING SENSOR ARRAY

TECHNICAL FIELD

The present invention relates to a technology for enabling high-sensitivity magnetic sensor, and in particular, relates to a diamond crystal and film that enables the high-sensitivity magnetic measurement at room temperature in the atmosphere, a magnetic sensor using the same, and the like.

BACKGROUND ART

Diamond can be said to be a specific crystal lattice in which a color center in a crystal behaves like so called "atoms (trapped atoms) in low temperature and a vacuum" in room temperature and the atmosphere. A nitrogen-vacancy complex (NV center) that is formed in the specific crystal lattice, or diamond, is one type of color center, and involves nitrogen (N) substituted with carbon and an atomic vacancy (V) that is positioned adjacent to this nitrogen, as is illustrated in FIG. 1, and has a spin S=1.

An $NV^-$ center, which is the NV center in a negatively charged state once it captures an electron, is only one solid characterized by the fact that a single spin can be operated and detected by light at room temperature and the coherence time is long, and is expected to be applied to a magnetic sensor having high spatial resolution and high sensitivity (see Non-Patent Literature 1 by D Le Sage et al., Non-Patent Literature 2 by J. R. Maze et al., and the like). There is a report that a magnetic detection limit of the sensor using the $NV^-$ center at ordinary temperature largely exceeds detection limits of a hole sensor and an impedance sensor, and is equivalent to the detection limit of SQUID, on a theoretical calculation (see Non-Patent Literature 3 by V. M. Acosta et al.).

FIG. 2 is a view for describing a principle of magnetic detection using the $NV^-$ center. The $NV^-$ center can take three electron spin states (triplet state) of $|0\rangle$, $|1\rangle$ or $|-1\rangle$, in a ground state. In the figure, $\Delta$ represents an energy difference between the $|0\rangle$ state and the $|\pm 1\rangle$ state, $\gamma$ represents a magnetic rotation ratio, and B represents magnetic field strength.

When the $NV^-$ center in the ground state is irradiated with green light, the $NV^-$ center emits red fluoresce. However, when it has the electron spin of $|1\rangle$ or $|-1\rangle$ in the ground state, some of the electrons after excitation pass through a singlet state and returns to the ground state, which makes it difficult to cause a fluorescence process. Energy separation ($2\gamma B$) between these electron spin states of $|1\rangle$ and $|-1\rangle$ is proportional to the magnetic field strength B, and accordingly when a sensor using the $NV^-$ center is irradiated with a microwave having a frequency of approximately 2.8 GHz, and the frequency of the microwave is swept, the sensor can detect the magnetic field strength as a brightness lowering point of the red fluorescence.

FIG. 3 is a view for conceptually describing that the brightness lowering point of the red fluorescence at the time when the frequency of the microwave has been swept varies depending on the magnetic field strength. This view, in which a horizontal axis is the frequency (GHz) of the microwave and a vertical axis is the brightness of the red fluorescence (arbitrary scale), conceptually shows that when the magnetic field B is changed in a range of 0 to 12 GHz, a split ($\Delta f$) between the frequencies (f1 and f2) of the microwave at the brightness lowering point of the red fluorescence increases proportionally to the magnetic field strength.

On the basis of such a principle, there is a reported result of measurement of a two-dimensional distribution of a weak magnetic field of approximately 1 mT (see Non-Patent Literature 4 by S. Hong), and there is also a report that a magnetic field of an fT level can be measured in principle (see Non-Patent Literature 3).

CITATION LIST

Patent Literature

Patent Literature 1: Japanese Patent Laid-Open No. 2012-110489
Patent Literature 2: Japanese Patent Laid-Open No. 2012-121747
Patent Literature 3: Japanese Patent Laid-Open No. 2012-121748

Non Patent Literature

Non-Patent Literature 1: D Le Sage et al. Nature Vol. 496, pp. 486-489 (2013)
Non-Patent Literature 2: J. R. Maze, et al. Nature Vol. 455, pp. 644-647 (2008)
Non-Patent Literature 3: V. M. Acosta et al., Phys. Rev. B Vol. 80, pp. 115202 (2009)
Non-Patent Literature 4: S. Hong, MRS BUL. Vol. 38 (February 2013)

SUMMARY OF INVENTION

Technical Problem

In recent years, there has been a need to measure magnetic fields in a wide range of regions two-dimensionally with high sensitivity, and it has been studied to use a color center including the above described $NV^-$ center in diamond, for magnetic sensing, as has been described above (see also Patent Literature 1: Japanese Patent Laid-Open No. 2012-110489, Patent Literature 2: Japanese Patent Laid-Open No. 2012-121747, and Patent Literature 3: Japanese Patent Laid-Open No. 2012-121748).

However, a technology for satisfying the need has not yet been established, and a further study is required on problems of, among others, what type of diamond is preferable to be used as a magnetic sensor, and what structure is preferable as a sensor array for two-dimensional high-sensitivity magnetic measurement.

The present invention has been made in consideration of such problems, and an object of the present invention is to provide a diamond crystal (or film) that enables two-dimensional magnetic sensor with higher sensitivity at room temperature in the atmosphere, and a diamond device, a magnetic sensor and a magnetic measurement device that use the same.

Solution to Problem

In order to solve the above described problems, a diamond crystal according to a first aspect of the present invention has an NV region that contains a complex (NV center) of nitrogen (N) substituted with a carbon atom and a vacancy (V) located adjacent to the nitrogen, on a surface or in the vicinity of the surface, wherein the NV region has a donor concentration equal to or higher than a concentration of the NV centers.

A diamond crystal according to a second aspect of the present invention has an NV region that contains a complex (NV center) of nitrogen (N) substituted with a carbon atom and a vacancy (V) located adjacent to the nitrogen, on a surface or in the vicinity of the surface, wherein a crystal face of the NV region is a {111} face or a face having an off-angle that is ±10 degrees or less against the {111} face, and a principal axis of the NV center is a <111> axis that is perpendicular to the {111} face.

The donor concentration is preferably in a range of $10 \times 10^{15}$ cm$^{-3}$ to $10 \times 10^{19}$ cm$^{-3}$. In addition, the NV region is preferably formed in a crystal film of nitrogen-doped diamond, which has been grown by a CVD method or a high-temperature high-pressure method (HPHT method).

An device using the diamond of a first aspect according to the present invention includes a second region formed so as to be in contact with a first region that contains a complex (NV center) of nitrogen (N) substituted with a carbon atom of the diamond and a vacancy (V) located adjacent to the nitrogen, and has a donor concentration higher than that in the first region.

It is preferable that the first regions are two-dimensionally and periodically arrayed in a plane, and second regions each having a donor concentration higher than that in the first region are formed on respective side faces or peripheries of the first regions.

In addition, it is preferable that the second region is formed of n-type diamond, and the first region is formed of i-type or p-type diamond. In another preferred aspect the second region is formed of the n-type diamond, and the first region is a depletion region formed by a p-n junction.

In addition, the second region has preferably an n$^+$ type of conductivity type of which the donor level is $1 \times 10^{18}$ cm$^{-3}$ or higher.

An device using the diamond of the second aspect according to the present invention includes an electrode for applying a positive potential that is provided through an insulating film, on one principal surface side of a first region that contains a complex (NV center) of nitrogen (N) substituted with a carbon atom of the diamond and a vacancy (V) located adjacent to the nitrogen.

It is preferable that the first regions are two-dimensionally and periodically arrayed in a plane, and the electrodes for applying the positive potential are provided on the respective one principal surface sides of the first regions, through an insulating film.

It is preferable that a second region that has an NV center concentration lower than that in the first region is formed so as to be in contact with the first region.

In addition, it is preferable that a crystal face of the first region is a {111} face or a plane having an off-angle that is ±10 degrees or less against the {111} face, and a principal axis of the NV center is a <111> axis that is perpendicular to the {111} face.

In addition, the first region has preferably a donor concentration equal to or higher than the concentration of the NV centers of the first region. In addition, the donor concentration is preferably in a range of $10 \times 10^{15}$ cm$^{-3}$ to $10 \times 10^{19}$ cm$^{-3}$.

In addition, it is preferable that the diamond is a diamond film that is formed on a substrate by a CVD method or a high-temperature high-pressure method (HPHT method).

Furthermore, it is preferable that the diamond device has further an electric field generating unit that has at least two electrodes that are provided so as to face each other, on upper and lower face sides or side face sides of the diamond crystal portion containing the first region.

In the diamond device according to the present invention, the periodic array of the first regions is, for instance, a square periodic array in which the center of the first region is positioned on each lattice point of a two-dimensional square lattice, when the plane is viewed from above.

In addition, in the diamond device according to the present invention, the periodic array of the first regions is, for instance, a hexagonal packed array in which on six vertexes of a regular hexagon that has a center point on a center position of a particular first region, the centers of the other first regions are positioned respectively, when the plane is viewed from above.

A magnetic sensor according to the present invention includes: the above described diamond device; and an optical sensor that detects an optical signal that is an optical signal emitted from the respective surfaces of the first regions in the diamond device and is generated originating from electron spin resonance in the NV center.

A magnetic measurement system according to the present invention is a magnetic measurement system provided with the above described magnetic sensor, and includes: a sample stage that is provided so as to face the diamond device; an optical system that irradiates the diamond device with green light; a microwave generating unit that irradiates the diamond device with a microwave of which a frequency is variable; and a signal processing unit that processes an optical signal that has been detected by the optical sensor and has been generated originating from electron spin resonance in the NV center.

The magnetic measurement system according to the present invention preferably further has an electric field generating unit that has at least two electrodes that are provided so as to face each other, on upper and lower face sides or side face sides of the diamond crystal portion containing the first region.

A method for manufacturing a sensor array of a first aspect according to the present invention includes: forming columnar portions that are two-dimensionally and periodically arrayed on the surface of a plate-like diamond, as first regions; forming a complex (NV center) of nitrogen (N) substituted with a carbon atom of the diamond and a vacancy (V) located adjacent to the nitrogen, in each of the first regions; and forming second regions that are second regions that surround respective peripheries of the first regions and each have a donor concentration higher than that in the first region. In addition, as another aspect, an electrode for applying a positive potential may be provided on a rear face side of the first region through an insulating film.

A method for manufacturing a sensor array of a second aspect according to the present invention includes forming a plurality of junctions of a heterogeneous conductivity type that is formed of diamond and has a complex (NV center) of nitrogen (N) substituted with a carbon atom of the diamond and a vacancy (V) located adjacent to the nitrogen, formed in a region of the junction, on a principal surface of a plate-like diamond. Incidentally, the aspect may be such an aspect of having means for injecting current into the junctions of the heterogeneous conductivity type or means for applying a voltage thereto.

Advantageous Effects of Invention

The diamond crystal according to the present invention enables almost 100% of the complex (NV center) of the nitrogen (N) substituted with the carbon atom and the vacancy (V) located adjacent to the nitrogen to be in a negatively charged state (NV$^-$). In addition, spin states of the NV$^-$ centers can be aligned in one direction, and as a result, a peak of an optically detected magnetic resonance (ODMR: Optically Detected Magnetic Resonance) signal becomes sharp, and besides, a contrast is also enhanced.

Furthermore, the diamond device according to the present invention can keep the NV center formed in the above described diamond crystal in a negatively charged state (NV$^-$).

As a result, the magnetic sensor that is provided with the diamond device according to the present invention enables two-dimensional magnetic measurement at ordinary temperature in the atmosphere to be carried out with high sensitivity as compared with a conventional one.

BRIEF DESCRIPTION OF DRAWINGS

FIG. 4 is a view showing a result obtained by measuring light emission (photoluminescence) emitted from a NV$^-$ center and a NV$^0$ center of an n-type diamond crystal (FIG. 4(A)) having a NV$^-$ center formed therein and an undoped diamond crystal (FIG. 4(B)) that have been irradiated with light having a wavelength of 532 nm, while being irradiated with light having a wavelength of 593 nm.

FIG. 6 is a view showing an experimental result confirming that as a result of the fact that the principal axes of the NV$^-$ centers, which are formed in the diamond thin film formed by a CVD method and has the principal surface of a (111) face, are aligned with the [111] axis, peak positions of optically detected magnetic resonance signals also become equal.

FIG. 9 is a view for describing one example of the band view of the sensor array of the first aspect according to the present invention.

FIG. 10 is a band view for describing a basic concept of a sensor array of a second aspect according to the present invention.

DESCRIPTION OF EMBODIMENTS

Figure 1:
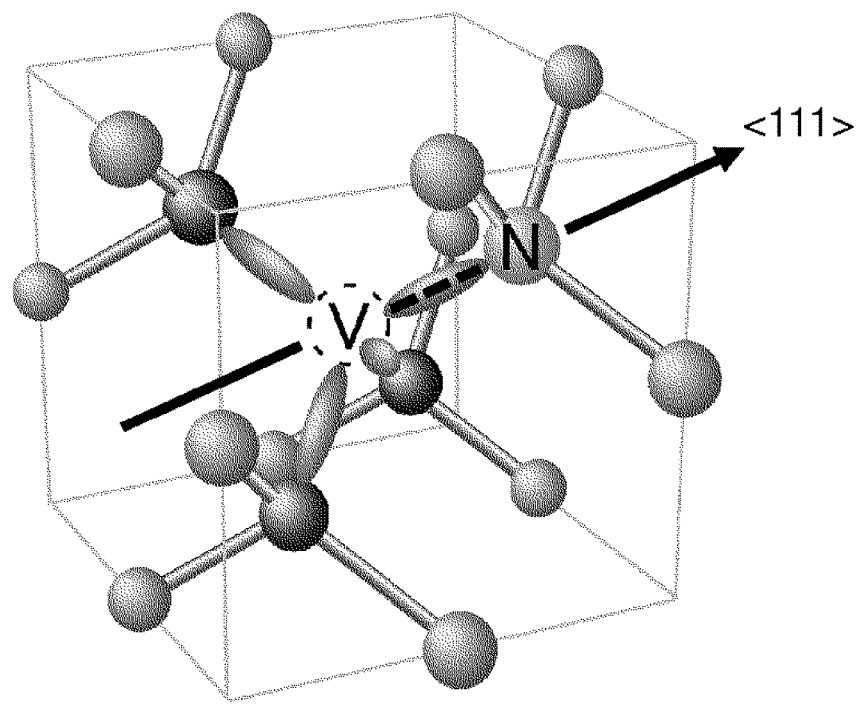
FIG. 1 is a view for describing a nitrogen-vacancy complex (NV center) formed in diamond.
Figure 2:
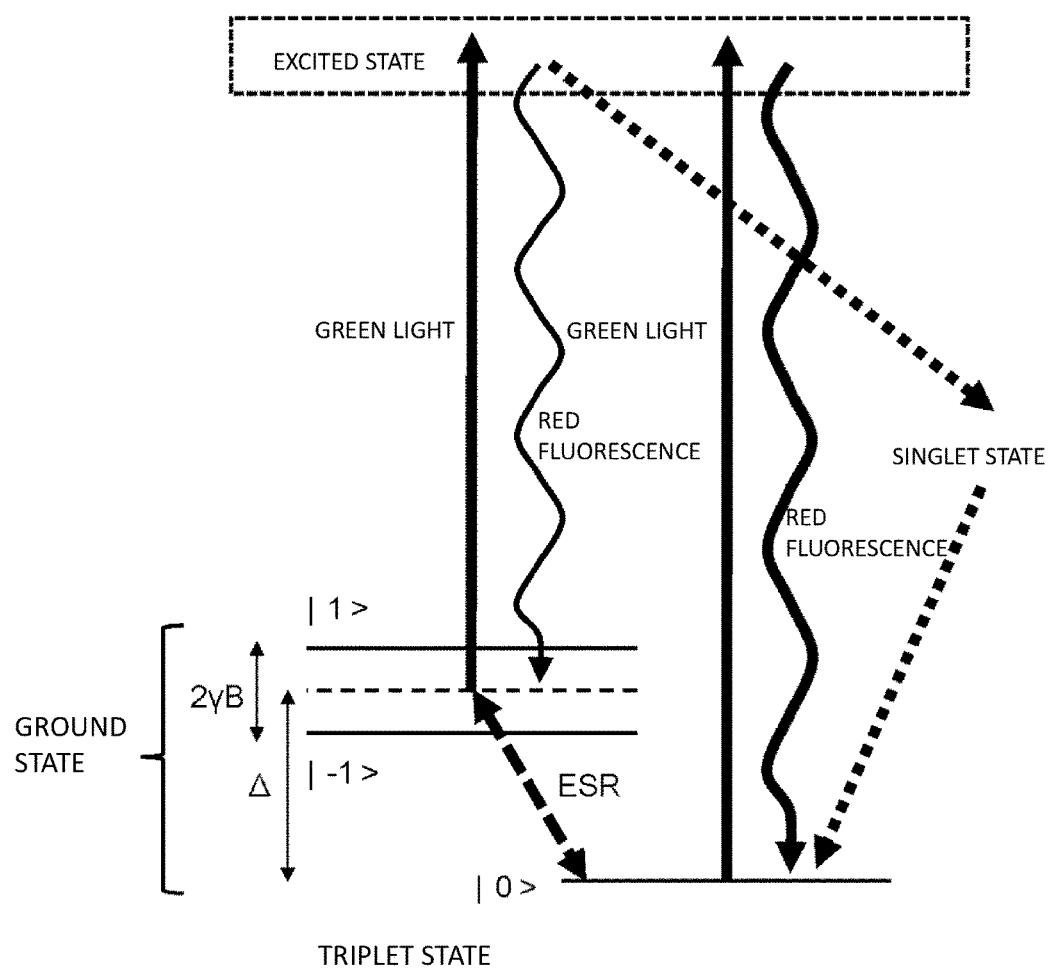
FIG. 2 is a view for describing a principle of magnetic detection using a NV$^-$ center.
Figure 3:
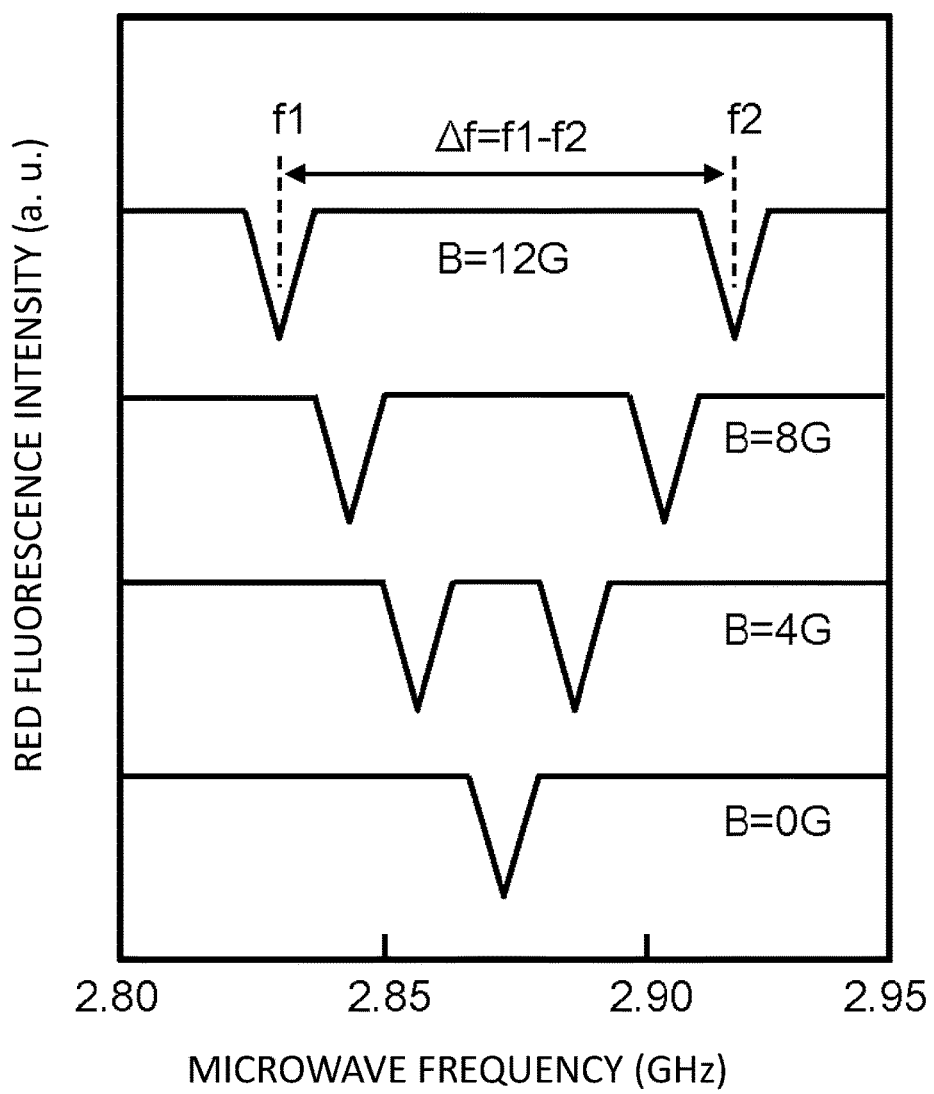
FIG. 3 is a view for conceptually of ODMR for describing that a brightness lowering point of red fluorescence at the time when a frequency of a microwave has been swept varies depending on magnetic field strength.

The diamond crystal, and the diamond device, the magnetic sensor and the magnetic measurement device that use the same, according to the present invention, will be described below with reference to the drawings.

Incidentally, the present invention is targeted at the diamond crystal, but a similar effect is also expected in another wide band-gap semiconductor such as silicon carbide. In addition, the diamond device according to the present invention will be described below as a sensor array having such a form that the first regions each containing the NV center are two-dimensionally and periodically arrayed in the plane, but the present invention is not limited to this form. The diamond device may have a single first region, and the application thereof is not limited to the sensor.

[Diamond Crystal] (First Aspect)

The diamond crystal of a first aspect according to the present invention is preferably a plate-like diamond crystal, and has an NV region that contains a complex (NV center) of nitrogen (N) substituted with a carbon atom and a vacancy (V) located adjacent to the nitrogen, at least on a surface or in the vicinity of the surface. The NV region has a donor concentration equal to or higher than a concentration of the NV centers.

In the case of a diamond crystal in which an electrical neutral NV$^0$ center is formed in an undoped diamond crystal and is negatively charged by a technique of forming a defect by irradiation with an electron beam or the like, and then subjecting the NV$^0$ center to heat treatment, or the like, and the NV$^-$ center is thus formed, it is known that when the diamond crystal is irradiated with light, a part of the NV$^-$ center becomes the NV$^0$ center, and a ratio between the NV$^-$ center and the NV$^0$ center after irradiation with light results in becoming approximately 7:3.

However, as a result of a study by the present inventors, it has become clear that in the case of the diamond crystal in which the above described NV$^-$ center is formed on the n-type diamond crystal, the film of which has been formed by the CVD method, even when the diamond crystal has been irradiated with light, the NV$^-$ center keeps the charged state, in other words, the NV$^-$ center stably exists even after having been irradiated with light.

FIG. 4 is a view showing a measurement result of light emission emitted from a NV⁻ center and a NV⁰ center of an n-type diamond crystal having a NV⁻ center formed therein (FIG. 4(A)) and an undoped diamond crystal (FIG. 4(B)) that have been irradiated with light having a wavelength of 532 nm, while being irradiated with light having a wavelength of 593 nm. In this figure, a horizontal axis shows the number of photons that have been observed during irradiation with light having a wavelength of 593 nm, and a vertical axis shows the number of events at the time when each of the number of the photons has been observed. From this measurement result, a ratio between the NV⁻ center and the NV⁰ center can be known that exist in the diamond crystal after irradiation with light. Incidentally, the result shown in FIG. 4(A) is a result obtained from an n-type diamond crystal that contains the NV⁻ centers in a concentration of approximately $1 \times 10^{11}$ cm$^{-3}$ and is doped with phosphorus (P) in a concentration of approximately $1 \times 10^{15}$ cm$^{-3}$.

It is understood that only signals emitted from the NV⁻ centers are observed from the n-type diamond crystal (FIG. 4(A)), and that the NV⁻ centers keep the charged state also after irradiation with light, in other words that the NV⁻ centers stably exist also after irradiation with light.

In contrast to this, from the undoped diamond crystal (FIG. 4(B)), signals emitted from the NV⁰ centers are observed in addition to the signals emitted from the NV⁻ centers, and the ratio (NV⁻ center: NV⁰ center) becomes 0.74:0.26. In other words, 26% of the NV⁻ centers in the undoped diamond crystal become the NV⁰ centers due to irradiation with light.

Such a phenomenon is understood to occur because even though some NV⁻ centers once emit electrons due to irradiation with light and become the NV⁰ centers, these NV⁰ centers capture electrons again that have been emitted from donors with which the diamond crystal has been doped, and become the NV⁻ centers again. Therefore, in order to make the NV⁻ centers stably exist even after irradiation with light, it is effective that the donor concentration in the crystal is equal to or higher than the concentration of the NV centers in the NV region.

The donor concentration in the NV region may be equal to or higher than the concentration of the NV centers in the region, is $1 \times 10^{12}$ cm$^{-3}$ or higher for instance, and is preferably in a range of $10 \times 10^{15}$ cm$^{-3}$ to $10 \times 10^{19}$ cm$^{-3}$, in order to achieve an efficient electron supply to the NV⁰ center.

In addition, the above described donor is generally phosphorus (P); but may be nitrogen (N) impurities that substitute for carbon and exist in the crystal as P1 centers (electric charge 0 and spin S=½); or may be arsenic (As) or sulfur (S); and besides may also be a complex of boron (B) and hydrogen (H), or the like.

Such a diamond crystal may be a natural diamond crystal, or may be a diamond that is artificially synthesized by a high-temperature high-pressure method (HPHT method) or a CVD method (chemical vapor deposition method) using a microwave plasma or the like, and may also be a thin film crystal, for instance, which has been grown on a diamond substrate by a method such as the CVD method. The diamond synthesized by the CVD method is easy to introduce a dopant such as phosphorus therein which becomes the n-type during growth, and can introduce also nitrogen therein which forms the NV center during film formation. Accordingly, it is effective to use the CVD method. In addition, this diamond crystal is preferably an Ib-type diamond crystal, and is preferably a single crystal from the viewpoint of aligning the face orientation of the above described NV region and having a long phase coherence time of the electron spin. However, even though the diamond crystal is a polycrystal or a nanocrystal, a similar effect can be obtained. The face orientation is preferably a {110} face, a {100} face and a {111} face, and is particularly preferably the {111} face, because of a reason that will be described later.

Incidentally, when considering the case where a nitrogen-doped diamond film is crystal-grown by a CVD method, it is practically useful in many cases that the face orientation is that of a crystal face having a slight off-angle from the {111} face. The off-angle in this case is appropriately determined, but is preferably ±10 degrees or less in general.

[Diamond Crystal] (Second Aspect)

A diamond crystal of a second aspect according to the present invention is preferably a plate-like diamond crystal, and has an NV region that contains a complex (NV center) of nitrogen (N) substituted with a carbon atom and a vacancy (V) located adjacent to the nitrogen, at least on a surface or in the vicinity of the surface. The crystal face of this NV region is a {111} face or a face having an off-angle that is ±10 degrees or less against the {111} face, and a principal axis of the NV center is a <111> axis that is perpendicular to the {111} face.

In other words, when the face orientation of the NV region is a (111) face, the principal axis of the NV center is the [111] axis that is perpendicular to the (111) face.

Also in this diamond crystal, the donor concentration in the NV region is equal to or higher than the concentration of the NV centers in the region, and is preferably in a range of $10 \times 10^{15}$ cm$^{-3}$ to $10 \times 10^{19}$ cm$^{-3}$, in order to achieve an efficient electron supply to the NV⁰ center. In addition, the NV region is formed in the crystal film of the nitrogen-doped diamond, which has been grown by the CVD method or the HPHT method, for instance.

As is shown in FIG. 1, the NV center in the diamond crystal has $C_{3v}$ symmetry of which the principal axis is the <111> axis, there exist four equivalent orientations, and dipoles result in being formed randomly with respect to the four equivalent <111> axes, on the basis of which carbon out of four carbons (C) that are adjacent to the vacancy (V) is substituted with nitrogen (N).

Figure 5:
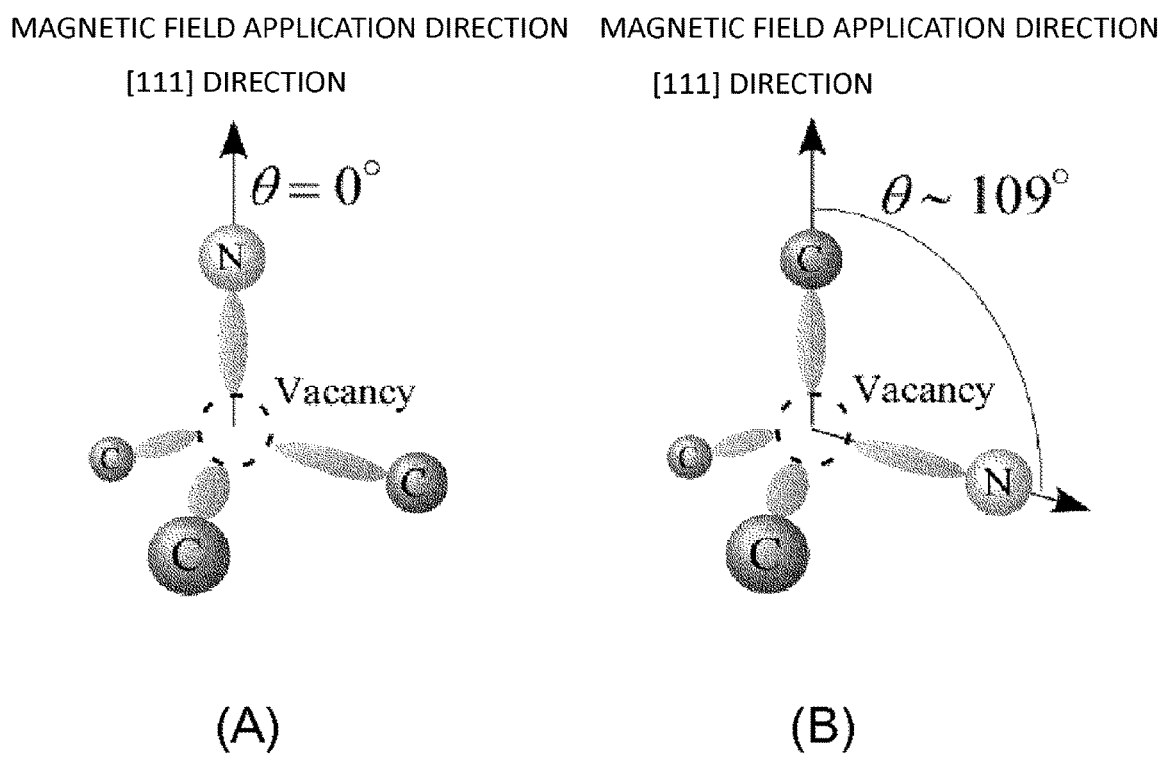
FIG. 5 is a view for describing a relationship between a magnetic field direction and a principal axis of the NV center, in the case where when the magnetic field is formed in the [111] direction, the principal axis of the NV center is in the same direction as the [111] direction ([111] direction) (FIG. 5(A)), and in the case where the principal axis of the NV center is in a <111> direction that is different from the [111] direction (FIG. 5(B)).

FIG. 5 is a view for describing a relationship between a magnetic field direction and a principal axis of the NV center, at the time when the magnetic field is formed in the [111] direction, in the case where the principal axis of the NV center exists in the same direction as the above direction ([111] direction) (FIG. 5(A)), and in the case where the principal axis of the NV center exists in a <111> direction that is different from the [111] direction (FIG. 5(B)). In the former case, an angle θ is 0, which is formed by the principal axis of the NV center (in other words, axis direction of dipole) and the magnetic field direction, and in the latter case, the angle θ becomes approximately 109 degrees.

If the dipoles are randomly formed with respect to the four <111> axes of which the dipoles are equivalent, and the above described four angles θ are different from each other, four lines of resonance lines result in appearing. If the magnetic field is formed in the [111] direction, one axis among the four equivalent <111> axes forms θ=0, and any one of the angles θ formed by the other three axes and the magnetic field direction becomes approximately 109 degrees. Because the three resonance frequencies become the same, the number of the resonance lines that appear in a spectrum becomes 2, and an intensity ratio between the two resonance lines becomes 1:3.

Thus, when the dipoles have been randomly formed, the intensity of fluorescence emitted from the diamond crystal tends to vary depending on light incident on the crystal, a direction of an external magnetic field and the like. For this reason, in order to achieve the high-sensitivity magnetic sensor using the NV⁻ center in the diamond crystal, it becomes necessary to align the spin states of the NV⁻ centers with one direction, in other words, to align the axes of the NV centers.

The present inventors have studied this point, and as a result, it has become clear that if the face orientation of the NV region is controlled to be the {111} face (or face having off-angle that is ±10 degrees or less against {111} face), the principal axis of the NV center can be aligned with the <111> axis that is perpendicular to the {111} face. Incidentally, hereafter, when the face is used, the {111} face is used as a meaning including also faces having off-angles that are ±10 degrees or less against the {111} face.

FIG. 6 is a view showing an experimental result confirming that as a result of the fact that the principal axes of the NV⁻ centers, which are formed in a diamond thin film formed by a CVD method and has the principal surface of the (111) face, are aligned with the [111] axis, peak positions of optically detected magnetic resonance (ODMR: Optically Detected Magnetic Resonance) signals also become equal.

As has been described above, such a diamond crystal does not need to be a crystal grown by the CVD method, and may also be a nitrogen-doped diamond crystal that has been grown by another method such as the HPHT method. In addition, the diamond crystal may be doped with nitrogen certainly while the crystal is grown, but may also be doped by an ion implantation method or the like after the crystal has been grown.

Table 1 is a table that organizes examination results on rates at which the NV center axes are aligned, for each method of synthesizing diamond (and nitrogen-doping method).

Any of samples A, B and D is a diamond that has been synthesized on a diamond substrate of which the principal surface is the (111) face, by the CVD method. Incidentally, as for conditions of the CVD operation, it is preferable that a methane dilution concentration for hydrogen is set at 0.25 to 1%, and a gas pressure, a power and a substrate temperature are set in ranges of 130 Torr to 20 kPa, 400 to 3,700 W and 850 to 1100° C., respectively.

In the samples A and D out of these samples, the NV centers have been formed by being doped with nitrogen while the crystal of the diamond has been grown. In addition, in the sample B, the NV centers have been formed by being doped with nitrogen (¹⁵N) by the ion implantation method after the crystal of the diamond has been grown. Incidentally, as for the ion implantation, it is preferable to implant the ¹⁵N ions in the substrate with an acceleration voltage of approximately 30 keV while annealing the substrate so that the substrate temperature becomes approximately 600° C. In addition, it is preferable to set the dose amount at $10^9$-$10^{16}$ cm⁻², and in order to reduce the crystal defect, further to perform annealing in an Ar atmosphere at a temperature of approximately 1,000° C. for approximately 2 hours after ion implantation.

The samples C and E are diamond that has been synthesized by an IIa HPHT method and an Ib HPHT method, respectively, and in the sample C, similarly to the sample B, the NV centers have been formed by being doped with the nitrogen (¹⁵N) by the ion implantation method, after the crystal of the diamond has been grown. In addition, in the sample E, the crystal of the diamond has been doped with nitrogen while the crystal has been grown, then the crystal of the diamond has been further grown, and the NV centers have been formed by irradiation with an electron beam. Incidentally, this irradiation with the electron beam has been performed on conditions that the acceleration voltage is 0.5 MeV and the concentration of the electron beam is $1.5 \times 10^{16}$ cm⁻², and in order to reduce the crystal defect, the annealing has been performed in the Ar atmosphere at a temperature of 1,000° C. for 2 hours, after irradiation with the electron beam.

According to the result shown in Table 1, in the samples A and D in which the NV centers have been formed by being doped with the nitrogen while the crystal of the diamond is grown, the NV center axes are aligned with the [111] direction at such a high ratio as to exceed 99%. Incidentally, in the table, an item described as "single" in the item of "NV center" means that the observed NV center has been single, and an item described as "ensemble" means that there have been many observed NV centers.

TABLE 1

| Sample | Synthesis method | Nitrogen-doping method | NV center | NV//[111] ratio |
|---|---|---|---|---|
| A | CVD | Grown-in | Single | >99% |
| B | CVD | Ion implantation | Single | 43% |
| C | IIa HPHT | Ion implantation | Single | 35% |
| D | CVD | Grown-in | Ensemble | >99% |
| E | Ib HPHT | Grown-in (Electron beam irradiation) | Ensemble | 43% |

FIG. 6(A) is a confocal laser fluorescence microscope image, and each of portions shown by a round mark in this figure is the single NV⁻ center. FIG. 6(B) shows ODMR signals emitted from these single NV⁻ centers, and signals having the peak at the same frequency are obtained from any of the single NV⁻ centers. Incidentally, 50 pieces of the single NV⁻ centers have been subjected to such the ODMR measurement, but similar spectrum to that shown in FIG. 6(B) has been obtained from any of the single NV⁻ centers. This result means that the principal axes of any of the single NV⁻ centers that are formed in the diamond thin film of which the principal surface is the (111) face are aligned with the [111] that is the <111> axis that is perpendicular to the (111) face. Incidentally, the spectrum in FIG. 6(B) is a measurement result of irradiation with a high frequency wave (2.55 to 2.85 GHz) and irradiation with the magnetic field of approximately 7 mT in the [111] direction, while observing the light emission from the single NV center by using the confocal laser microscope, at room temperature.

As has been described above, the NV center in the diamond crystal has the $C_{3v}$ symmetry of which the principal axis is the <111> axis, and in the case where the dipoles have been randomly formed with respect to the four equivalent <111> axes, the ODMR signal also varies depending on the direction of the magnetic field that is applied to the NV center. For instance, if the magnetic field has been applied from four different directions of a [111] direction, a [1−1−1] direction, a [−11−1] direction and a [−1−11] direction, the ODMR signals that are obtained under each of the magnetic field application conditions result in being different from each other. Incidentally, in the above described marking, "−1" means "1 bar."

However, when the face orientation of the NV region is controlled to the {111} face and the principal axes of the NV centers are aligned with the <111> axis that is perpendicular to the {111} face, even though the magnetic field has been applied from the above described four different directions, a depression frequency (resonance frequency) of the ODMR signal becomes the same, as is shown in FIG. 6(B).

FIG. 7(A) is a view showing ODMR signals that have been obtained from samples in which the NV⁻ centers have been formed into comparatively high concentration (approximately $1 \times 10^{14}$ cm$^{-3}$) in the diamond thin film formed by a CVD method and has the principal surface of the (111) face; a horizontal axis shows a microwave frequency (MHz) and a vertical axis shows the intensity of the ODMR red fluorescence (arbitrary scale). The principal axes of the NV⁻ centers that have been formed in the diamond thin film become the <111> axis that is perpendicular to the above described {111} face. In other words, any of the principal axes of the NV⁻ centers are aligned with the <111> axis that is perpendicular to the {111} face. When the principal axes of the NV⁻ centers are aligned with the <111> axis that is perpendicular to the above described {111} face, even though the application direction of the magnetic field has been shifted from the <111> axis direction that is perpendicular to the {111} face, a plurality of signals do not appear, as is shown in (a) and (b) of FIG. 7(B).

Figure 7:
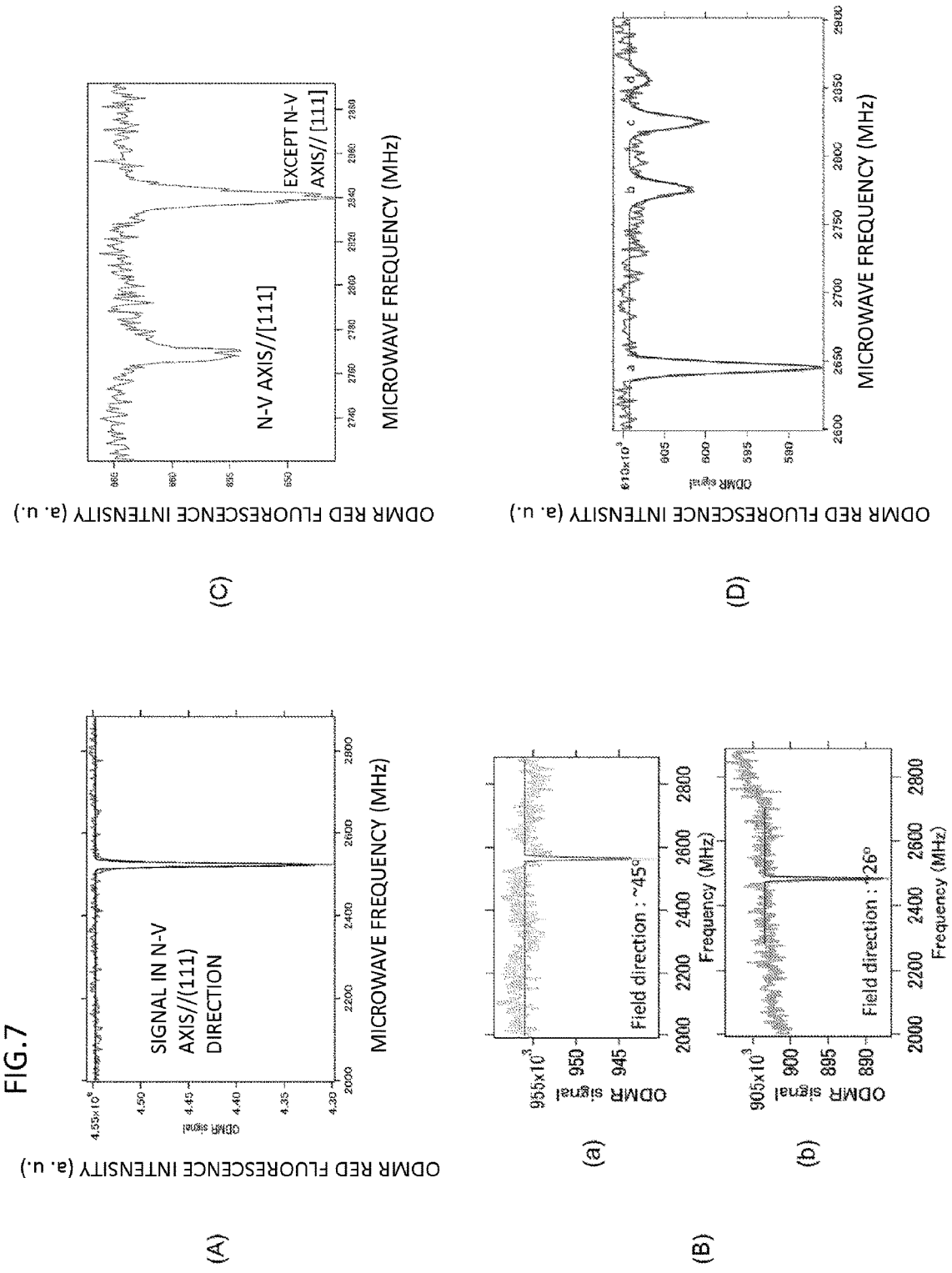
FIG. 7 is a view showing ODMR signals that have been acquired from samples in which the NV$^-$ centers have been formed into high concentration in the diamond thin film formed by a CVD method and has a principal surface of the (111) face.

However, when the dipoles are randomly formed with respect to the four equivalent <111> axes of the NV centers, the signal emitted from the NV⁻ center having the <111> axis that is perpendicular to the {111} face is different from signals emitted from the NV⁻ centers having the three <111> axes except the axis, as is shown in FIG. 7(C). In addition, when the application direction of the magnetic field is shifted from the direction of the <111> axis that is perpendicular to the {111} face, the four ODMR signals that are divided from each other result in appearing, as is shown in FIG. 7 (D).

Incidentally, the spectra in FIGS. 7(A) to (D) are the measurement results of irradiation with a high frequency wave (2.55 to 2.85 GHz) and irradiation with the magnetic field of approximately 16 mT in the [111] direction, while observing the light emission emitted from the single NV center by using the confocal laser microscope, at room temperature.

The sample is obtained in which the above described principal axes of the NV centers are aligned with the particular <111> axis (here, [111] axis) out of the four equivalent <111> axes, in the following way, for instance. Nitrogen gas, methane gas and hydrogen gas are introduced into a reaction chamber, and there, a film is formed on a diamond substrate that is synthesized by a high-temperature high-pressure method, is an Ib-type and has the (111) face (off-angle is 10 degrees or less), in the plasma with a microwave CVD method. The CVD conditions shall be the followings, for instance: a total gas pressure is 25 Torr; a flow rate of the gas is 400 sccm; a power of the microwave is 750 W; and a mixture ratio of the methane and the hydrogen is approximately 0.05%. In addition, the substrate temperature shall be approximately 800° C. The diamond film that has been obtained by such the CVD method is oriented mainly to the (111) face, and the NV centers are formed in the film, of which the principal axes are [111] that is the <111> axis that is perpendicular to this (111) face. Incidentally, it is desirable to introduce the nitrogen during film formation.

Such a diamond crystal may be a diamond crystal of which the principal surface is the {111} face; may be a natural diamond or a diamond that is synthesized by the high-temperature high-pressure method (HPHT) or also by the CVD method using the microwave plasma, or is also artificially synthesized; and is preferably an Ib-type diamond crystal that can be obtained, for instance, by a process of homoepitaxially growing the diamond thin film on a diamond substrate of which the principal surface is the {111} face, with the CVD method. In addition, the diamond thin film is desirably a single crystal, but a polycrystal or a nanodiamond can also provide a similar effect. It is desirable to introduce the nitrogen at the time of the CVD film formation, but it is also possible to introduce the nitrogen by ion implantation after film formation.

Also in such the diamond crystal of the second aspect, it is preferable that the NV region has the donor concentration equal to or higher than the concentration of the NV centers. In addition, the donor concentration in the NV region may be equal to or higher than the concentration of the NV centers in the region, and for instance, is $1 \times 10^{12}$ cm$^{-3}$ or higher.

Furthermore, the above described donor is generally phosphorus (P); but may be nitrogen (N) impurities that substitute for carbon and exist in the crystal as P1 centers (electric charge 0 and spin S=½); or may be arsenic (As) or sulfur (S); and besides may also be a complex of boron (B) and hydrogen (H), or the like.

[Sensor Array] (First Aspect)

A sensor array of a first aspect according to the present invention is an device using diamond, wherein a second region formed so as to be in contact with a first region that contains a complex (NV center) of nitrogen (N) substituted with a carbon atom of the diamond and a vacancy (V) located adjacent to the nitrogen, and has a donor concentration higher than that in the first region. It is preferable that the first regions are two-dimensionally and periodically arrayed in a plane, and second regions each having a donor concentration higher than that in the first region are formed on respective side faces or peripheries of the first regions.

Due to such a form, an energy band of the first region is curved by existence of the second region, and this band curvature facilitates electron injection caused by diffusion from the second region. An electron that has been injected into the first region is captured by the NV center (NV⁰ center) that is in an electrically neutral state in the first region, and shows an effect of suppressing the lowering of the density of the NV centers in the negatively charged state (NV⁻ centers), which enable magnetic detection to have high spatial resolution and high sensitivity.

Figure 8:
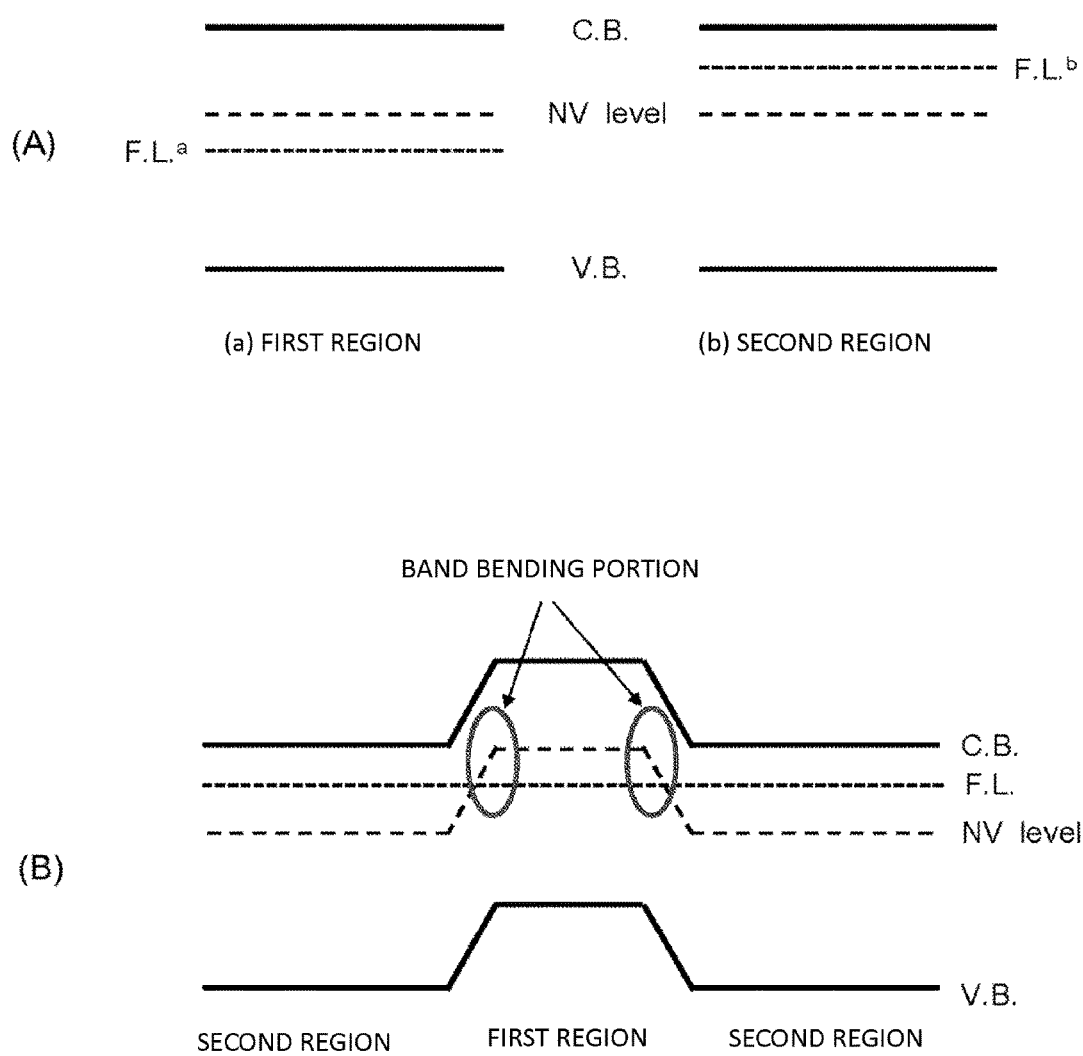
FIG. 8 is a band view for describing a basic concept of a sensor array of a first aspect according to the present invention.

FIG. 8 is a band view for describing a basic concept of the sensor array of the first aspect according to the present invention.

Incidentally, here, it is supposed that the above described first region is almost undoped p⁻ type diamond, and the second region that surrounds the first region is n⁺ type diamond. However, the sensor array of the first aspect according to the present invention may be a sensor array in which the energy band of the first region is curved by the existence of the second region, and this band curvature induces electron injection due to diffusion from the second region. Accordingly, for instance, the sensor array may be a sensor array in which the second region is formed of n⁻ type diamond and the first region is formed of i-type or p-type diamond. In addition, the sensor array may be a sensor array in which the second region is formed of the n-type diamond and the first region is a depletion region formed by a p-n junction. In essence, the sensor array may have a form in which a heterogeneous conductivity type of junction is formed in which a complex (NV center) of nitrogen (N) substituted with a carbon atom of diamond and a vacancy (V) located adjacent to the nitrogen is formed in the region of the junction, and the depletion region is formed in this junction.

In (a) and (b) of FIG. 8(A), the respective band views of the n⁻ type diamond and the n⁺ type diamond are shown, and an energy level (NV⁻ level) of the NV⁻ center that is formed at least in the first region is positioned in the band gap of the diamond crystal.

When the first region (n⁻ type) having the band view shown in (a) of FIG. 8(A) is surrounded by the second region (n⁺ type) having a donor concentration higher than that in the first region as shown in (b) of FIG. 8(A), the energy band in the first region is curved in a boundary region between the first region and the second region, as is shown in the band view in FIG. 8(B).

The NV⁻ center formed in the diamond crystal is considered to be stable at room temperature, but when the NV⁻ center has been affected by disturbance such as irradiation with light, the captured electron is emitted and the NV⁻ center tends to become the NV⁰ center. When the NV⁻ center has become the NV⁰ center, the NV⁰ center results in remaining in the crystal as it is, until the NV⁰ center captures the electron again.

In order to convert such the NV⁰ center into the NV center again which can detect magnetism at high spatial resolution and with high sensitivity as the NV⁻ center, it is necessary for the NV⁰ center to capture the electron In the present invention, the second region surrounds the first region, which has a donor concentration higher than that in the first region, and thereby curves the energy band in the first region. Due to this band curvature, the electron is injected from the second region by diffusion, and thereby the above described NV⁰ center is enabled to capture the electron.

Incidentally, in the conceptual view shown in FIG. 8, the curvature of the energy band is formed only in the boundary region between the first region and the second region, but it is possible to cause the curvature of the energy band substantially in the whole region within the first region, by narrowing the width of the first region, or by using a p-type layer of low concentration or an i-layer for the first region. In other words, it is possible to achieve "depletion" in the whole width of the first region by narrowing the width of the first region.

FIG. 9 is a view for describing one example of the band view of the sensor array of the first aspect according to the present invention. In the example shown in this figure, the i-type (or p-type of low concentration: p⁻ type) is used for the first region, this first region is surrounded by the n⁺ type of second region, and the curvature of the energy band is formed substantially in the whole region within the first region (FIG. 9(A)). Such a curvature of the energy band can be achieved, as is shown in FIG. 9(B), by forming a columnar pillar ((a) of FIG. 9(B)) in which the first region formed of the i-type (or p⁻ type of low concentration) exists in the center portion, and the second region formed of the n⁺ type exists in the periphery; by forming a prismatic pillar ((b) of FIG. 9(B)) in which the first region formed of the i-type (or p⁻ type of low concentration) exists in the center portion, and the second region of the n⁺ type exists in the periphery; or by a similar process.

For instance, in the case where the donor concentration of the second region is approximately $1 \times 10^{18}$ cm⁻³ and the acceptor concentration of the first region is approximately $1 \times 10^{16}$ cm⁻³, depletion layers of approximately 0.5 μm are formed in the first region side from both boundaries between the first region and the second region, respectively. Accordingly, when the width of the first region is set at approximately 1.0 μm, the above described effect can be shown in almost the whole region of the first region. In addition, in the case where the acceptor concentration of the first region is approximately $1 \times 10^{17}$ cm⁻³, the width of the first region is controlled to approximately 0.4 μm; and in the case where the acceptor concentration of the first region is approximately $3 \times 10^{16}$ cm⁻³, the width of the first region is controlled to approximately 0.7 μm. Then, the above described effect can be shown in almost the whole region of the first region.

Also in the sensor array of such an aspect, it is preferable to control the face orientation of the first region to the {111} face, and to align the principal axes of the NV centers with the <111> axis that is perpendicular to the {111} face.

In addition, it is preferable that the first region has a donor concentration equal to or higher than the concentration of the NV centers in the first region, and that the second region has the n⁺ type conductivity type of which the donor level is $1 \times 10^{18}$ cm⁻³ or higher.

In this case, the donor is generally phosphorus (P); but may be nitrogen (N) impurities that substitute for carbon and exist in the crystal as P1 centers (electric charge 0 and spin S=½); or may be arsenic (As) or sulfur (S); and besides may also be a complex of boron (B) and hydrogen (H), or the like.

In addition, it is preferable that the concentration of the NV centers in the second region is lower than the concentration of the NV centers in the first region.

In addition, it is preferable that the above described diamond is, for instance, a nitrogen-doped diamond film that has been formed on a substrate by a CVD method. Such a diamond film is obtained, for instance, in the following way. Nitrogen gas, methane gas and hydrogen gas are introduced into a reaction chamber, and there, a film is formed on a diamond substrate that is synthesized by a high-temperature high-pressure method, is an Ib-type and has the (111) face (off-angle is 10 degrees or less), in the plasma with a microwave CVD method. As for the CVD conditions, for instance, a total gas pressure shall be 25 Torr, a flow rate of the gas shall be 400 sccm, a power of the microwave shall be 750 W, and a mixture ratio between the methane and the hydrogen shall be approximately 0.05%. In addition, the substrate temperature shall be approximately 800° C. The diamond film that has been obtained by such the CVD method is oriented mainly to the (111) face, and the NV center is formed in the film, of which the principal axis is [111] that is the <111> axis that is perpendicular to this (111) face. Incidentally, it is desirable to introduce the nitrogen during film formation.

Furthermore, the sensor array may have a form in which each of the first regions has an electrode for applying a positive potential provided on one principal surface side (rear face side), through an insulating film. When such the electrode is provided and the positive potential is applied thereto, such a probability that the NV⁰ center thereby captures an electron again can be enhanced, similarly to the above described curvature effect of the energy band. This point will be described later.

A method for manufacturing the above described sensor array of the first aspect includes: for instance, forming columnar portions that are two-dimensionally and periodically arrayed on the surface of a plate-like diamond, as first regions; forming the complex (NV center) of nitrogen (N) substituted with the carbon atom of the diamond and the vacancy (V) located adjacent to the nitrogen, in each of the first regions; and forming second regions that are second regions that surround respective peripheries of the first regions and have the donor concentration higher than that in the first region to curve the energy band of the first region as has been described above.

[Sensor Array] (Second Aspect)

A sensor array of a second aspect according to the present invention is an device using diamond, wherein an electrode for applying a positive potential is provided through an insulating film, on one principal surface side (rear face side) of the first region that contains a complex (NV center) of nitrogen (N) substituted with a carbon atom of the diamond and a vacancy (V) located adjacent to the nitrogen. It is preferable that the first regions are two-dimensionally and periodically arrayed in a plane, and the electrodes for applying the positive potential are provided on the respective one principal surface sides (rear face sides) of the first regions, through the insulating film. In addition, it is preferable that a second region that has an NV center concentration lower than that in the first region is formed so as to be in contact with the first region.

FIG. 10 is a band view for describing a basic concept of the sensor array of the second aspect according to the present invention. Also here, it is supposed that the above described first region is almost undoped n⁻ type diamond.

The electrode is provided on the rear face side of the first region having a band view shown in FIG. 10(A) through an insulating film such as an oxide film. When the positive potential is applied to this electrode, the energy band in the first region is curved in the vicinity of an interface between the first region and the insulating film, as is shown in the band view of FIG. 10(B).

As has been described above, when the NV⁻ center formed in the diamond crystal has been affected by disturbance such as irradiation with light, there is a tendency that the electron that has been captured is emitted and the NV⁻ center becomes the NV⁰ center.

In the sensor array of the second aspect according to the present invention, the positive potential is applied to the electrode, and thereby curves the energy band of the first region in the vicinity of the interface between the first region and the insulating film to enhance such a probability that the NV⁰ center captures an electron again.

Also in the sensor array of such an aspect, it is preferable to control the face orientation of the first region to the {111} face, and to align the principal axes of the NV centers with the <111> axis that is perpendicular to the {111} face.

In addition, it is preferable that the first region has the donor concentration equal to or higher than the concentration of the NV centers in the first region.

In this case, the donor is generally phosphorus (P); but may be nitrogen (N) impurities that substitute for carbon and exist in the crystal as P1 centers (electric charge 0 and spin S=½); or may be arsenic (As) or sulfur (S); and besides may also be a complex of boron (B) and hydrogen (H), or the like.

In addition, it is preferable that the concentration of the NV centers in the second region is lower than the concentration of the NV centers in the first region.

In addition, it is preferable that the above described diamond is, for instance, a diamond thin film that has been formed on a substrate by a CVD method.

A method for manufacturing the above described sensor array of the second aspect includes: for instance, forming columnar portions that are two-dimensionally and periodically arrayed on the surface of a plate-like diamond, as first regions; forming a complex (NV center) of nitrogen (N) substituted with a carbon atom of the diamond and a vacancy (V) located adjacent to the nitrogen, in each of the first regions; forming second regions that are second regions that surround respective peripheries of the first regions and each have an NV center concentration lower than that in the first region; and providing electrodes for applying a positive potential on the respective rear face sides of the first region, through an insulating film.

Example of Process for Manufacturing Sensor Array: Example 1

Figure 11:
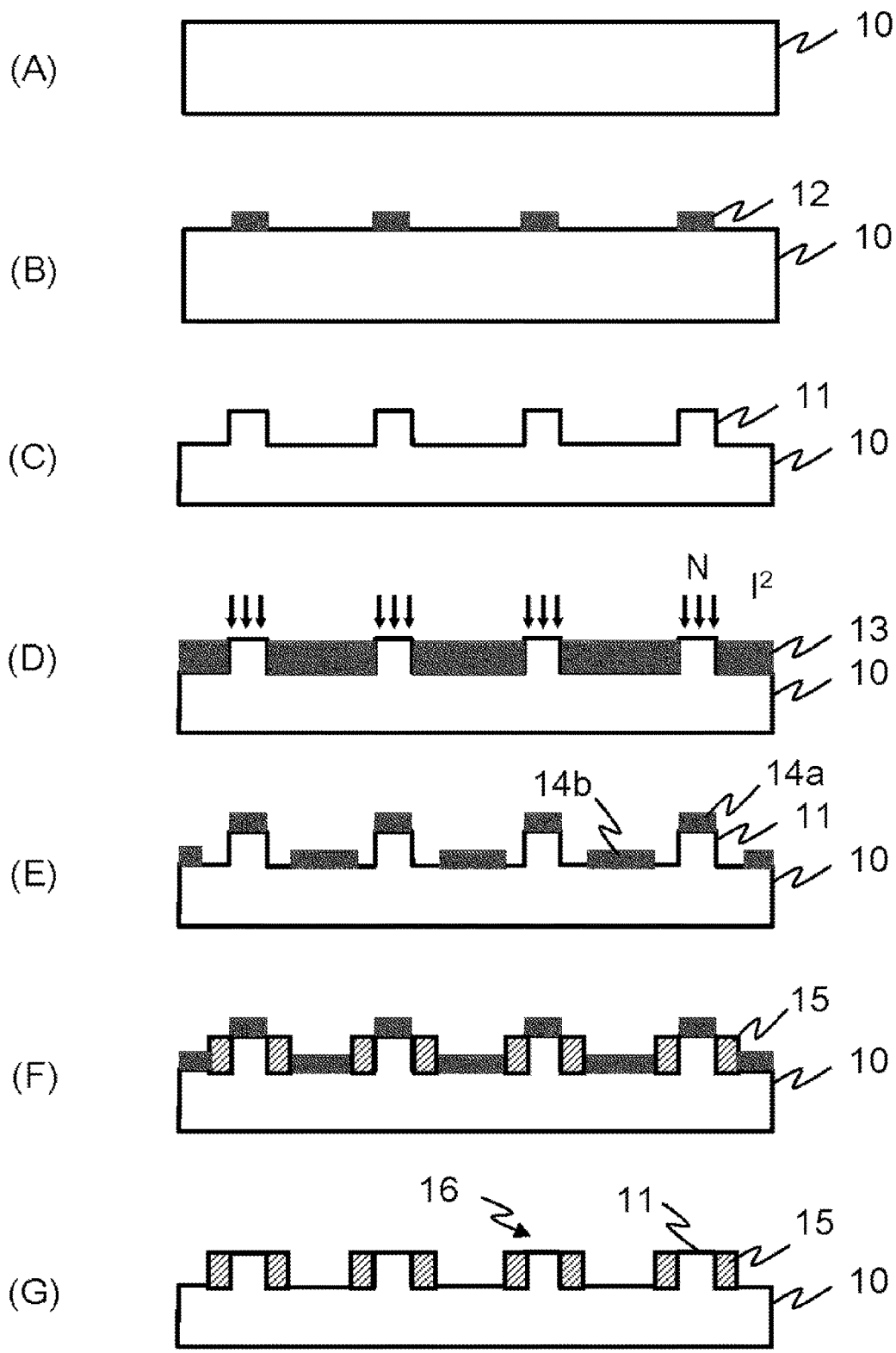
FIG. 11 is a view for conceptually describing an example of a first process for manufacturing the sensor array according to the present invention.

FIG. 11 is a view for conceptually describing an example of a process for manufacturing a sensor array according to the present invention.

Firstly, a diamond substrate 10 of which the principal surface is the (111) face is prepared (FIG. 11(A)), and a first mask 12 is formed on the principal surface of this diamond substrate 10 so that the above described first regions are two-dimensionally and periodically arrayed in a plane (FIG. 11(B)). Then, the peripheries of the regions that have been covered with this first mask 12 are removed by etching, and columnar portions 11 are formed that are two-dimensionally and periodically arrayed (FIG. 11(C)). Incidentally, this substrate 10 is a p-type single crystal diamond substrate that is doped, for instance, with boron (B); and in the case of the p-type, is preferably a p⁻ type (for instance, substrate having dope amount of $10 \times 10^{16}$ cm⁻³ or less in terms of boron concentration), or is more preferably a substrate (i-type) having resistivity close to that of an intrinsic semiconductor.

Subsequently, an ion of nitrogen (N) is implanted in the columnar portion 11 in such a state that the surface of the substrate in the periphery of the columnar portion 11 is protected by the second mask 13, and the NV center is formed in the columnar portion 11 that will become the first region (FIG. 11(D)). Incidentally, in the step of this ion implantation, it is also possible to form single NV centers on the columnar portions 11, respectively. Incidentally, even though the nitrogen (N) is introduced into the whole substrate that does not have the second mask 13 formed thereon, a similar effect is obtained.

After the second mask 13 has been removed, the surface of the columnar portions 11 and a partial region of the surface of the diamond substrate 10 are protected with third masks 14a and 14b (FIG. 11(E)), crystals of the n⁺ type diamond that is doped with phosphorus (P) are grown in the peripheries of the columnar portions 11 with the CVD method (FIG. 11(F)), and after that, the third masks 14a and 14b are removed. Then, a sensor array is obtained in which the first regions each containing the NV center are two-dimensionally and periodically arrayed in a plane in a state of each being surrounded by the second region 15 (FIG. 11(G)).

Incidentally, in the process example shown in FIG. 11, in order to suppress interference between pillars 16 that are formed of the columnar portions 11 that become the first region and of the second regions 15 that surround the columnar portions 11, respectively, the pillars 16 are intended to be separated from each other, and partial regions on the surface of the diamond substrate 10 shall be protected with the third mask 14b. For instance, when the width of the columnar portion 11 that becomes the first region is approximately 0.5 μm, a distance between the pillars 16 is set at approximately 1 μm.

Example of Process for Manufacturing Sensor Array: Example 2

Figure 12:
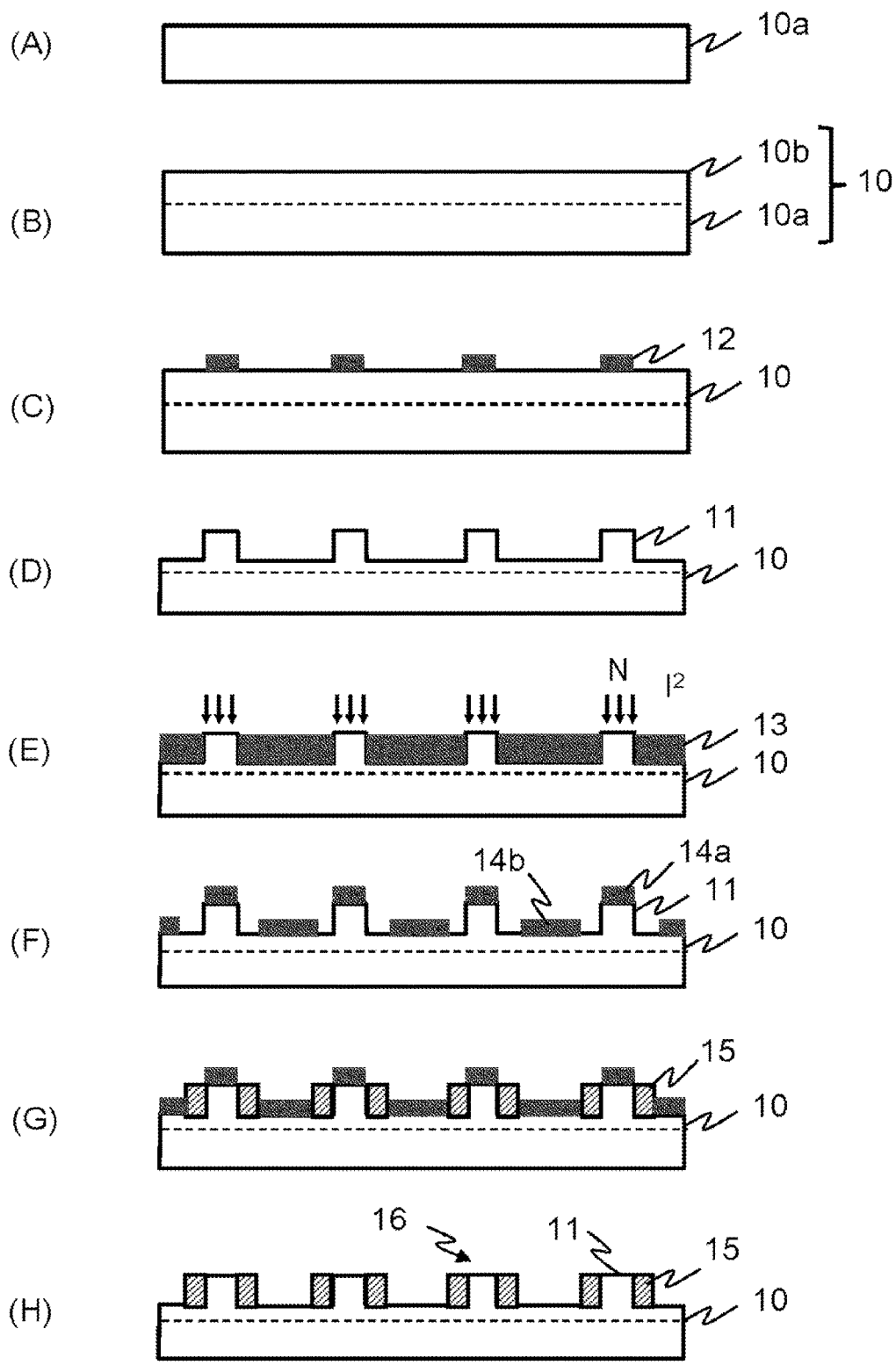
FIG. 12 is a view for conceptually describing an example of a second process for manufacturing the sensor array according to the present invention.

FIG. 12 is a view for conceptually describing an example of another process for manufacturing a sensor array according to the present invention.

A single crystal diamond substrate 10a is prepared of which the principal surface is the (111) face (FIG. 12(A)), and on the principal surface of this diamond substrate 10a, a single crystal diamond thin film 10b of which the conductivity type is, for instance, a p-type (or i-type) is formed by the CVD method (FIG. 12(B)). Incidentally, in the case of the p-type, the single crystal diamond thin film 10b is preferably a p⁻ type (for instance, thin film having dope amount of $10 \times 10^{16}$ cm$^{-3}$ or less in terms of boron concentration), or preferably has the resistivity that is close to that of an intrinsic semiconductor. This diamond substrate 10a and the diamond thin film 10b correspond to the above described diamond substrate 10.

Subsequent steps are similar to the steps described with reference to FIG. 11, and includes: forming a first mask 12 on the principal surface of the diamond substrate 10 (FIG. 12(C)), in order to two-dimensionally and periodically array the first regions in the plane; and removing the peripheries of the regions that are covered with this first mask 12 by etching to form columnar portions 11 that are two-dimensionally and periodically arrayed (FIG. 12(D)).

The steps subsequently include: protecting the surface of the substrate in the peripheries of the columnar portions 11 with a second mask 13; implanting ions of nitrogen (N) in the state to form the NV centers in the columnar portions 11 that become the first region (FIG. 12(E)); removing the second mask 13; then protecting the surface of the columnar portions 11 and partial regions of the surface of the diamond substrate 10 with third masks 14a and 14b (FIG. 12(F)); growing crystals of the n⁺ type diamond that is doped with phosphorus (P), in the peripheries of the columnar portions 11, with the CVD method (FIG. 12(G)); and then removing the third masks 14a and 14b to obtain a sensor array in which the first regions each containing the NV center are two-dimensionally and periodically arrayed in a plane, in a state of being surrounded by the second regions 15 (FIG. 12(H)).

Here, the shape of the above described columnar portion is not limited in particular, and the cross section may be a rectangle or a circle. However, from the viewpoint of isotropy, the cross section is preferably the circle, in other words, the pillar 16 has preferably a columnar shape.

The above described periodic array of the first regions is, for instance, a square periodic array in which the center of the first region is positioned on each lattice point of a two-dimensional square lattice, when the surface of the diamond is viewed from above.

In addition, the above described periodic array of the first regions is, for instance, a hexagonal packed array in which on six vertexes of a regular hexagon that has a center point on a center position of a particular first region, the centers of the other first regions are positioned respectively, when the surface of the diamond is viewed from above.

Example of Process for Manufacturing Sensor Array: Example 3

Figure 13:
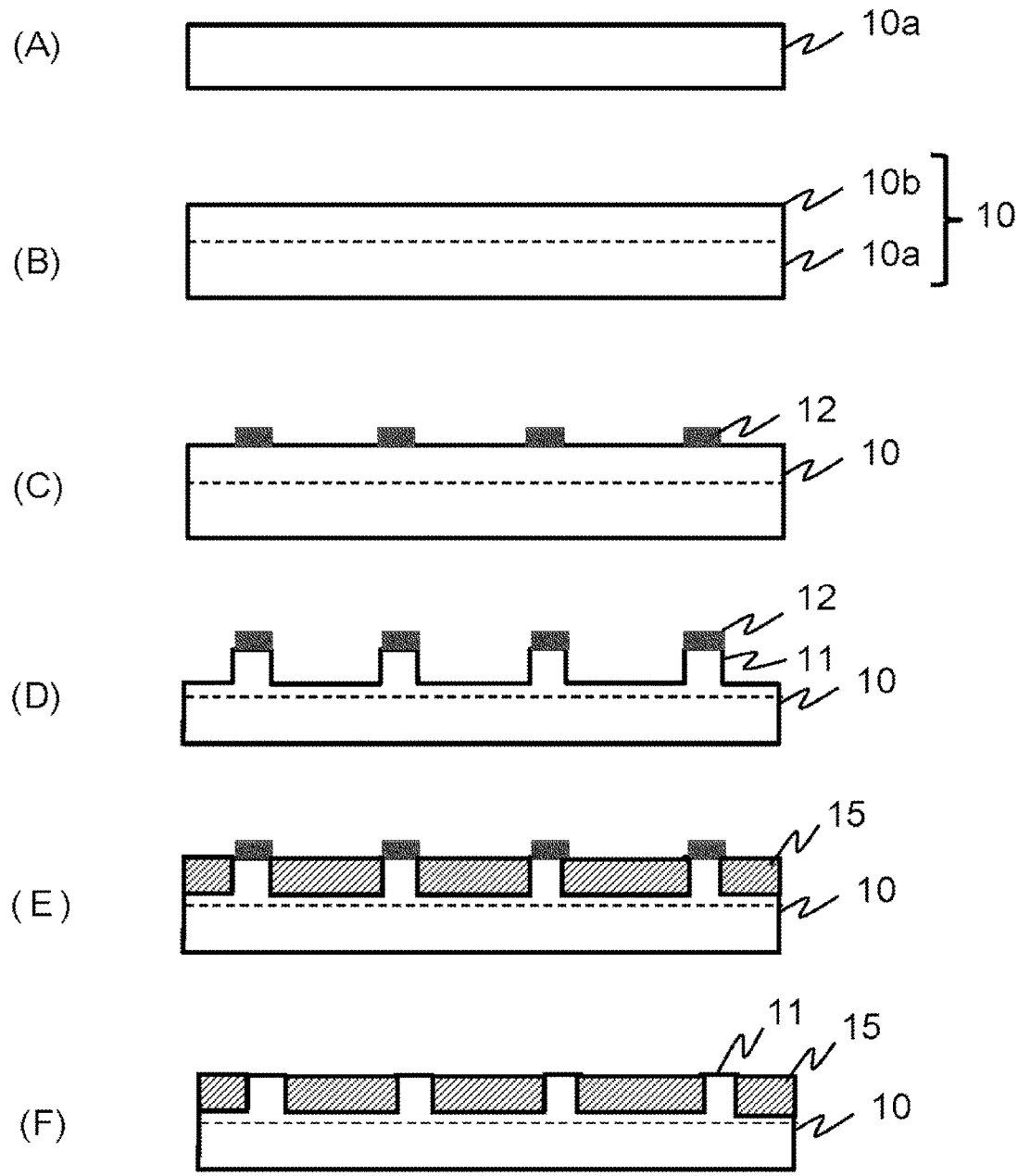
FIG. 13 is a view for conceptually describing an example of a third process for manufacturing the sensor array according to the present invention.

FIG. 13 is a view for conceptually describing an example of another process for manufacturing a sensor array according to the present invention. In this process example, the NV center is not formed by the ion implantation method, but is formed by being doped with nitrogen, while the single crystal diamond thin film 10b is formed by the CVD method.

A single crystal diamond substrate 10a is prepared of which the principal surface is the (111) face (FIG. 13(A)), and a single crystal diamond thin film 10b that is doped with the nitrogen (N) and has the principal surface of the (111) face is formed on the principal surface of this diamond substrate 10a, with the CVD method (FIG. 13(B)). This diamond substrate 10a and the diamond thin film 10b correspond to the above described diamond substrate 10. A mixed gas of hydrogen, methane and nitrogen is used as a process gas, for film formation of the single crystal diamond thin film 10b. Nitrogen is taken in during a CVD reaction, and the NV center is already formed in the single crystal diamond thin film 10b after the film formation. Incidentally, it is acceptable to irradiate the single crystal diamond thin film 10b with an electron beam, or implant ions of helium in the thin film, and then anneal the resultant thin film, in order to further increase the concentration of the NV centers in the single crystal diamond thin film 10b.

Subsequently, a first mask 12 is formed on the principal surface of the diamond film 10b so as to two-dimensionally and periodically array the first regions in a plane (FIG. 13(C)); the peripheries of the regions that are covered with this first mask are removed by etching; and columnar portions 11 are formed that are two-dimensionally and periodically arrayed (FIG. 13(D)). After this, crystals of n⁺ type diamond that is doped with phosphorus (P) are grown in the peripheries of the columnar portions 11 with the CVD method, and the second region 15 is formed (FIG. 13(E)), while the above described first mask 12 is not removed. After that, the first mask 12 is removed, and then a sensor array is obtained in which the first regions 11 each containing the NV center are two-dimensionally and periodically arrayed in the plane, in a state of being surrounded by the second region 15 (FIG. 13(F)).

Example of Process for Manufacturing Sensor Array: Example 4

As has been described above, the sensor array according to the present invention may be a sensor array in which the energy band of the first region is curved by the existence of the second region, and this band curvature induces electron injection due to diffusion from the second region. Accordingly, the sensor array may have a form in which the second region is formed of the n-type diamond, and the first region is a depletion region formed in a heterogeneous conductivity type of junction that includes a p-n junction. Such a heterogeneous conductivity type of junction will be described below as a so-called p-n junction, but may be a "p-n junction" or an "i-n junction". In addition, the sensor array may have a form of having means for injecting current into the junctions of the heterogeneous conductivity type, or means for applying a voltage thereto.

Such a sensor array can be manufactured by forming a plurality of p-n junctions on the principal surface of the plate-like diamond, which are p-n junctions formed of diamond and each have the complex (NV center) of nitrogen (N) substituted with a carbon atom of the diamond and a vacancy (V) located adjacent to the nitrogen, formed in a depletion region formed in the p-n junction.

Figure 14:
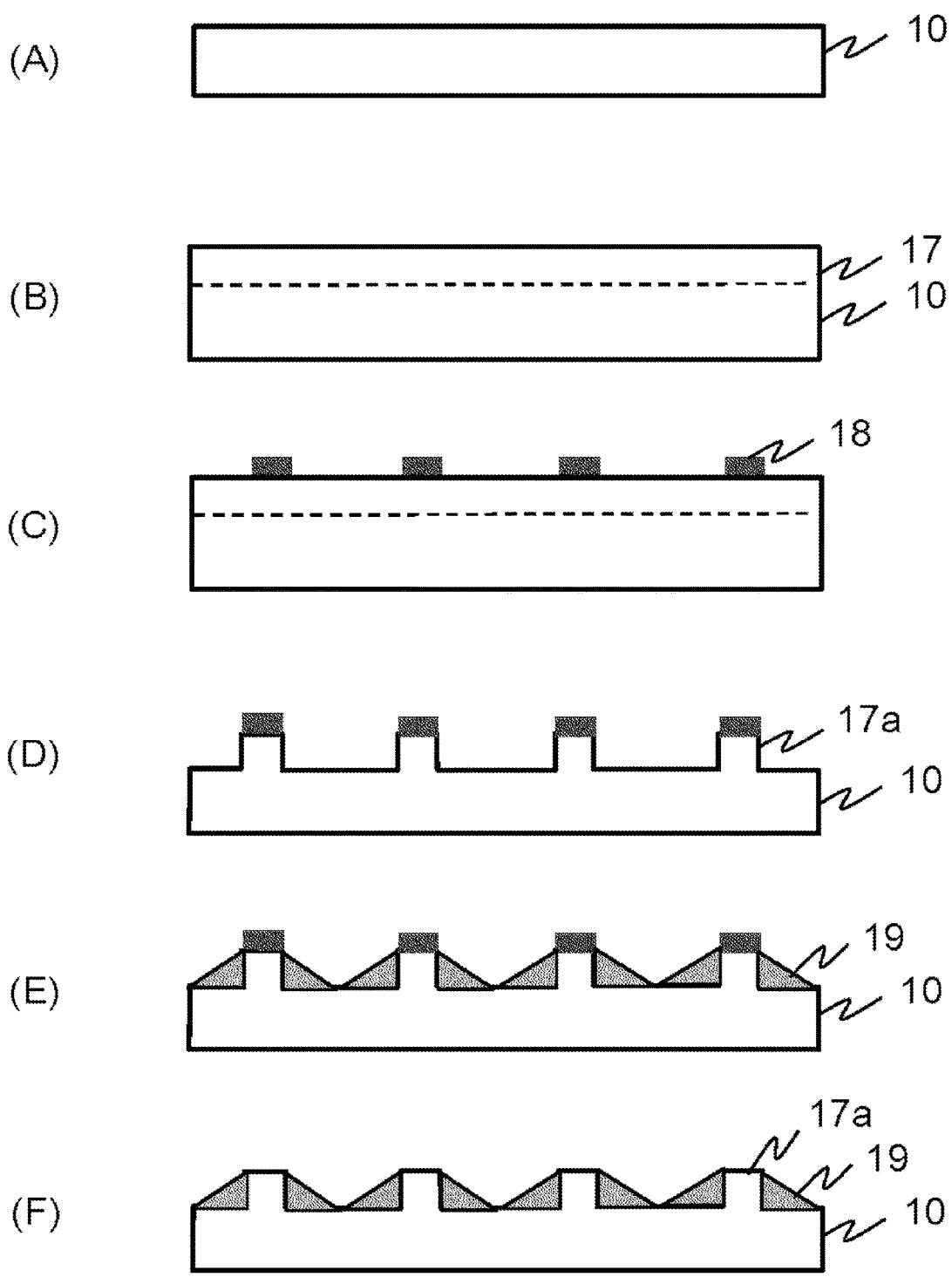
FIG. 14 is a view for conceptually describing an example of a fourth process for manufacturing the sensor array according to the present invention.

FIG. 14 is a view for conceptually describing an example of a process for manufacturing such a sensor array. A single crystal diamond substrate 10 is prepared of which the principal surface is the (100) face (FIG. 14(A)), and on the principal surface of this diamond substrate 10, a single crystal diamond thin film 17 of which the conductivity type is, for instance, a p-type (or i-type) is formed by the CVD method (FIG. 14(B)). Incidentally, in the case of the p-type, the single crystal diamond thin film 10b is preferably a p⁻ type (for instance, thin film having dope amount of $10 \times 10^{16}$ cm$^{-3}$ or less in terms of boron concentration), or preferably has the resistivity that is close to that of an intrinsic semiconductor. A mixed gas of hydrogen, methane and nitrogen is used as a process gas in film formation of the single crystal diamond thin film 17. In this case, the nitrogen (N) for forming the NV center is introduced into the film during a CVD process. The method is not limited to the above method, and the NV center can be formed in the film also by nitrogen ion implantation that is carried out after the CVD film has been formed.

Subsequently, a mask 18 is formed on the principal surface of the p-type diamond film 17 (FIG. 14(C)), the peripheries of the regions that are covered with this mask 18 are removed by etching, and columnar portions 17a are formed that are two-dimensionally and periodically arrayed (FIG. 14(D)). After this, crystals of n$^+$ type diamond 19 that is doped with phosphorus (P) are grown in the peripheries of the columnar portions 17a with the CVD method, and the second regions are formed (FIG. 14(E)), while the above described mask 18 is not removed. After that, the mask 18 is removed, and then a sensor array is obtained that has a plurality of p-n junctions formed on the principal surface of the plate-like diamond, which are p-n junctions formed of diamond and each have the complex (NV center) of nitrogen (N) substituted with a carbon atom of the diamond and a vacancy (V) located adjacent to the nitrogen, formed in a depletion region formed in the p-n junction (FIG. 14(F)).

Figure 15:
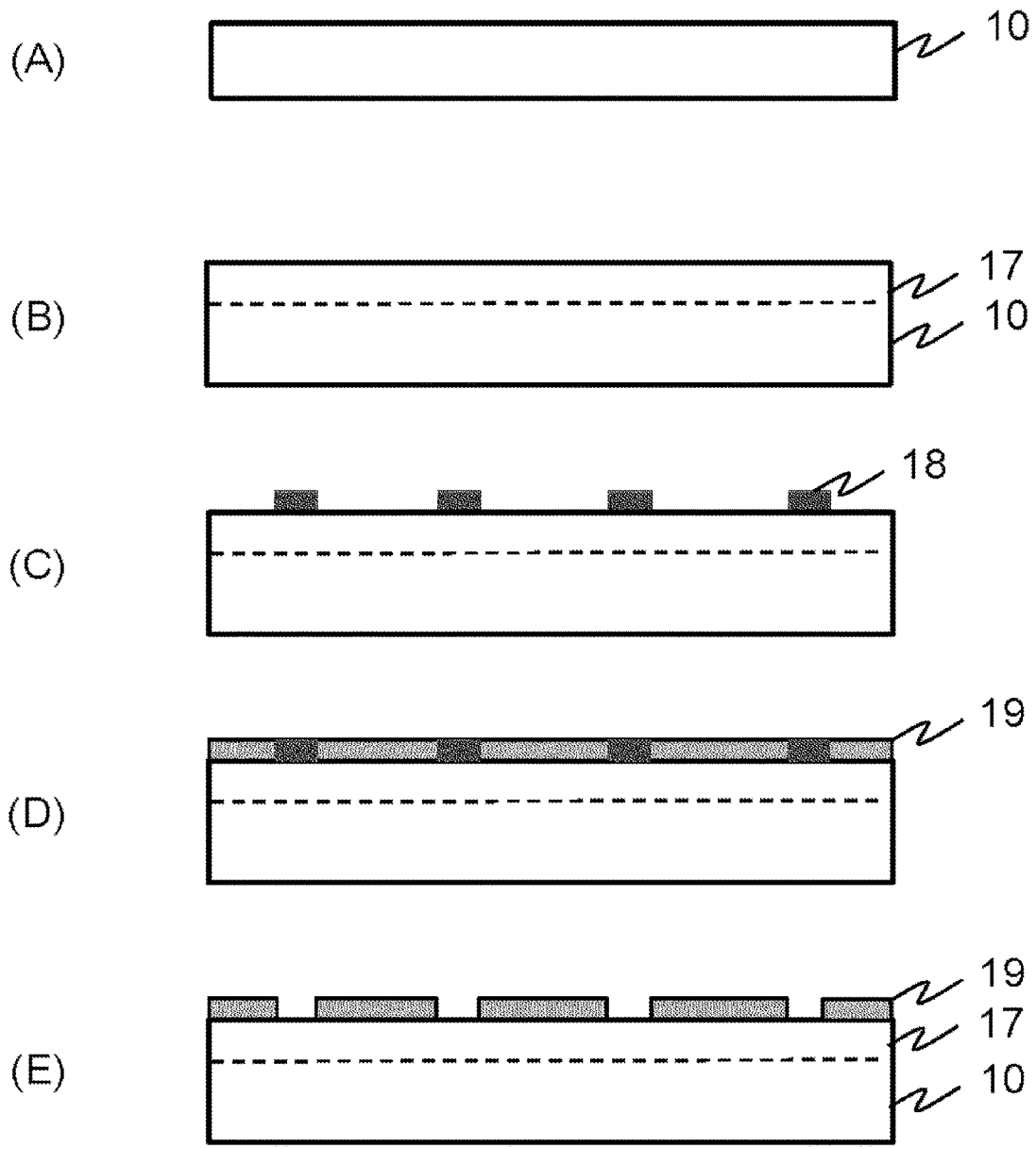
FIG. 15 is a view for conceptually describing another example of the fourth process for manufacturing the sensor array according to the present invention.

FIG. 15 is also a view for conceptually describing an example of a process for manufacturing the above described sensor array. A single crystal diamond substrate 10 is prepared of which the principal surface is the (111) face (FIG. 15(A)), and on the principal surface of this diamond substrate 10, a single crystal diamond thin film 17 of which the conductivity type is, for instance, a p-type (or i-type) is formed by the CVD method (FIG. 15(B)). Incidentally, in the case of the p-type, the single crystal diamond thin film 10b is preferably a p$^-$ type (for instance, thin film having dope amount of $10 \times 10^{16}$ cm$^{-3}$ or less in terms of boron concentration), or preferably has the resistivity that is close to that of an intrinsic semiconductor. A mixed gas of hydrogen, methane and nitrogen is used as a process gas for film formation of the single crystal diamond thin film 17. In this case, the nitrogen (N) for forming the NV center is introduced into the film during a CVD process. The method is not limited to the above method, but the NV center can be formed in the film also by nitrogen ion implantation that is carried out after the CVD film has been formed.

Subsequently, a mask 18 is formed on the principal surface of the p-type diamond film 17 (FIG. 15(C)), crystals of n$^+$ type diamond 19 that is doped with phosphorus (P) are grown in the peripheries of the regions that are covered with this mask 18, with the CVD method, and second regions are formed (FIG. 15(D)). After that, the mask 18 is removed, and then a sensor array is obtained that has a plurality of p-n junctions formed on the principal surface of the plate-like diamond, which are p-n junctions formed of diamond and each have the complex (NV center) of nitrogen (N) substituted with a carbon atom of the diamond and a vacancy (V) located adjacent to the nitrogen, formed in a depletion region formed in the p-n junction (FIG. 15(E)).

Figure 16:
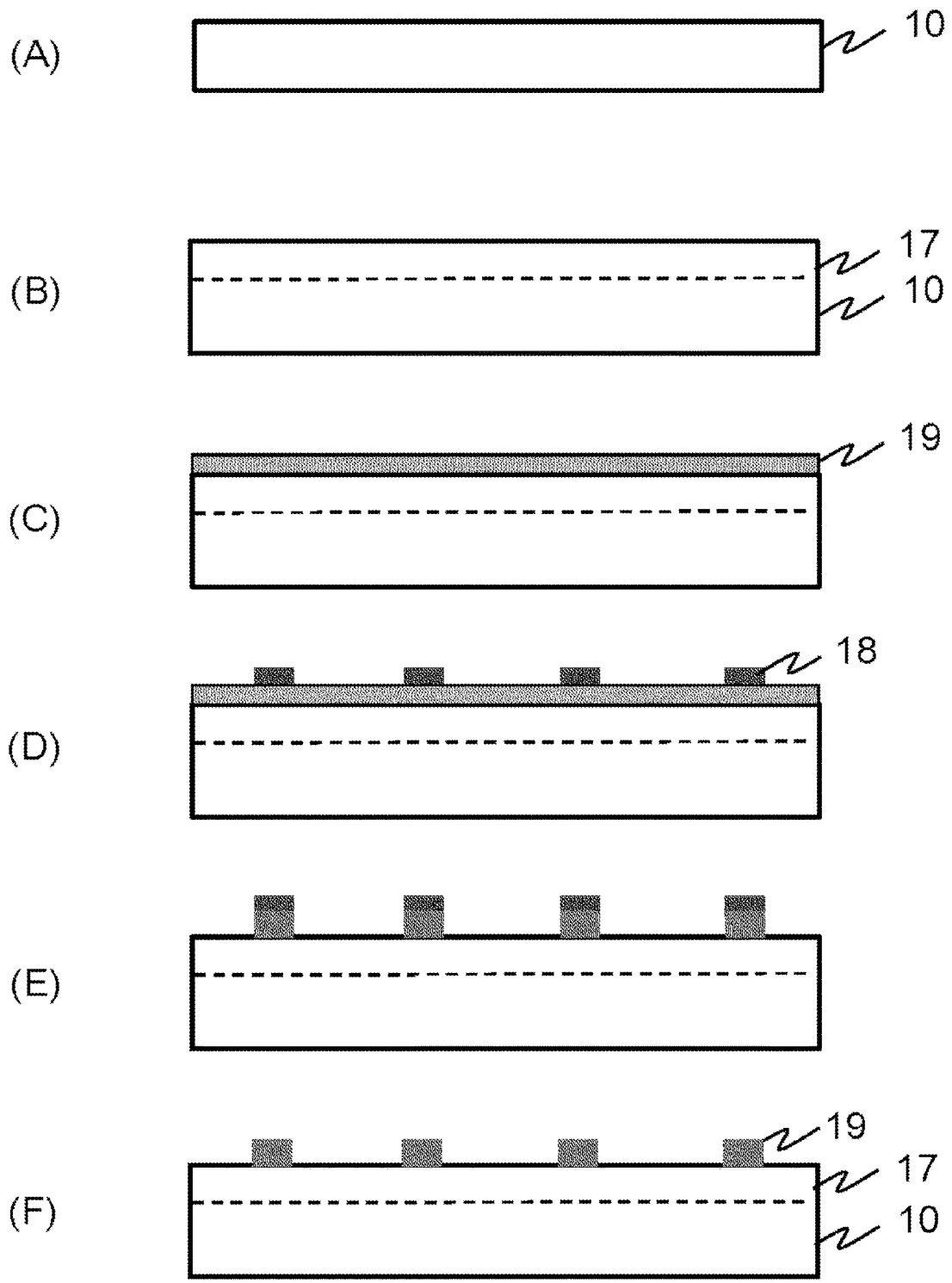
FIG. 16 is a view for conceptually describing another example of the fourth process for manufacturing the sensor array according to the present invention.

FIG. 16 is also a view for conceptually describing an example of a process for manufacturing the above described sensor array. A single crystal diamond substrate 10 is prepared of which the principal surface is the (111) face (FIG. 16(A)), and on the principal surface of this diamond substrate 10, a single crystal diamond thin film 17 of which the conductivity type is, for instance, a p-type (or i-type) is formed by the CVD method (FIG. 16(B)). Incidentally, in the case of the p-type, the single crystal diamond thin film 10b is preferably a p$^-$ type (for instance, thin film having dope amount of $10 \times 10^{16}$ cm$^{-3}$ or less in terms of boron concentration), or preferably has the resistivity that is close to that of an intrinsic semiconductor. A mixed gas of hydrogen, methane and nitrogen is used as a process gas for film formation of the single crystal diamond thin film 17. In this case, the nitrogen (N) for forming the NV center is introduced into the film during a CVD process. The method is not limited to the above method, and the NV center can be formed in the film also by nitrogen ion implantation that is carried out after the CVD film has been formed.

Subsequently, an n$^+$ type of single crystal diamond thin film 19 that is doped with phosphorus (P) is formed on the principal surface of the p-type diamond film 17 with the CVD method (FIG. 16(C)), a mask 18 is formed on the principal surface of the n-type of single crystal diamond thin film 19 (FIG. 16(D)), and the peripheries of the regions that are covered with this mask 18 are removed by etching (FIG. 16(E)). After that, the mask 18 is removed, and then a sensor array is obtained that has a plurality of p-n junctions formed on the principal surface of the plate-like diamond, which are p-n junctions formed of diamond and each have the complex (NV center) of nitrogen (N) substituted with a carbon atom of the diamond and a vacancy (V) located adjacent to the nitrogen, formed in a depletion region formed in the p-n junction (FIG. 16(F)).

It is obvious for those skilled in the art that even by a process except the illustrated processes in FIGS. 14 to 16, a sensor array is obtained that has the plurality of above described p-n junctions.

[Magnetic Measurement Device]

A magnetic sensor that is used in a magnetic measurement device according to the present invention includes: the above described sensor array 20; and an optical sensor 21 that detects an optical signal that is an optical signal emitted from the respective surfaces of the first regions in the sensor array and is generated originating from electron spin resonance in the NV center.

Figure 17:
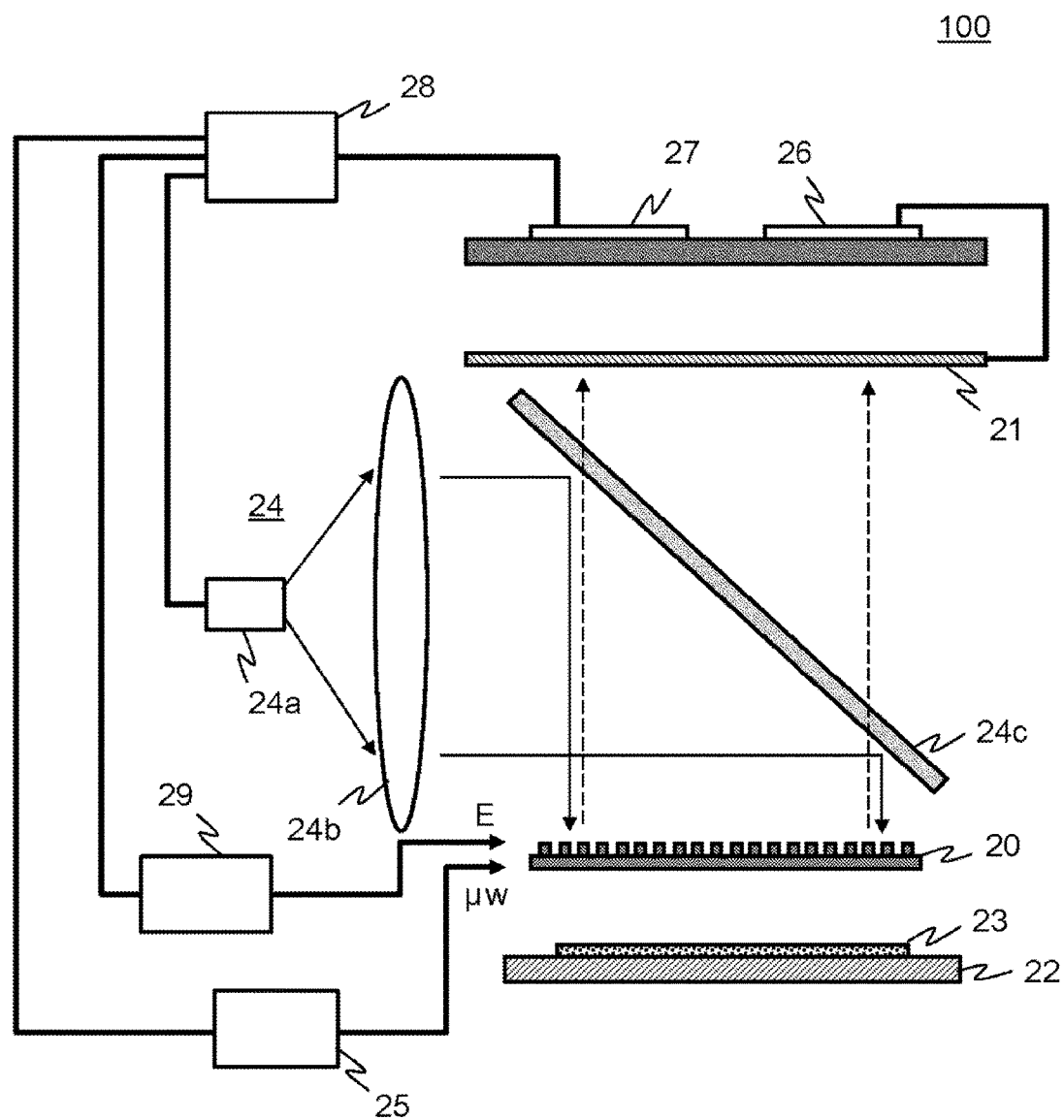
FIG. 17 is a block diagram for describing an outline of a configuration example of a magnetic measurement system according to the present invention.

FIG. 17 is a block diagram for describing an outline of a configuration example of the magnetic measurement device according to the present invention. This magnetic measurement device includes: a sample stage 22 for mounting a specimen 23, which is provided so as to face the sensor array 20; an optical system 24 that irradiates the sensor array 20 with green light; a microwave generating unit 25 that irradiates the sensor array 20 with a microwave of which the frequency is variable; and a signal processing unit 26 that processes the optical signal that has been detected by the optical sensor 21 and has been generated originating from electron spin resonance in the NV center.

In the configuration example shown in this figure, the optical system 24 is provided with a light source 24a, an irradiation lens 24b and a dichroic mirror 24c. From the light source 24a, green light of 638 nm is emitted in response to a signal emitted from a control circuit 28 that is connected to a module 27 that serves as a microwave source and a sensor interface, and the green light irradiates the sensor array 20 that is positioned in the lower part, through the dichroic mirror 24c.

The microwave of which the frequency is variable irradiates the sensor array 20 through the microwave generating unit 25, in response to the signal emitted from the control circuit 28 that is connected to the module 27.

Incidentally, FIG. 17 shows an aspect in which an electric field generating unit 29 for applying an electric field to the sensor array 20 is provided in the magnetic measurement device 100, but may be an aspect in which the electric field generating unit 29 is not provided therein.

Such an electric field generating unit 29 is an electric field generating unit that has at least two electrodes that are provided so as to face each other, for instance, on upper and lower face sides or side face sides of the diamond crystal portion containing the first region.

Figure 18:
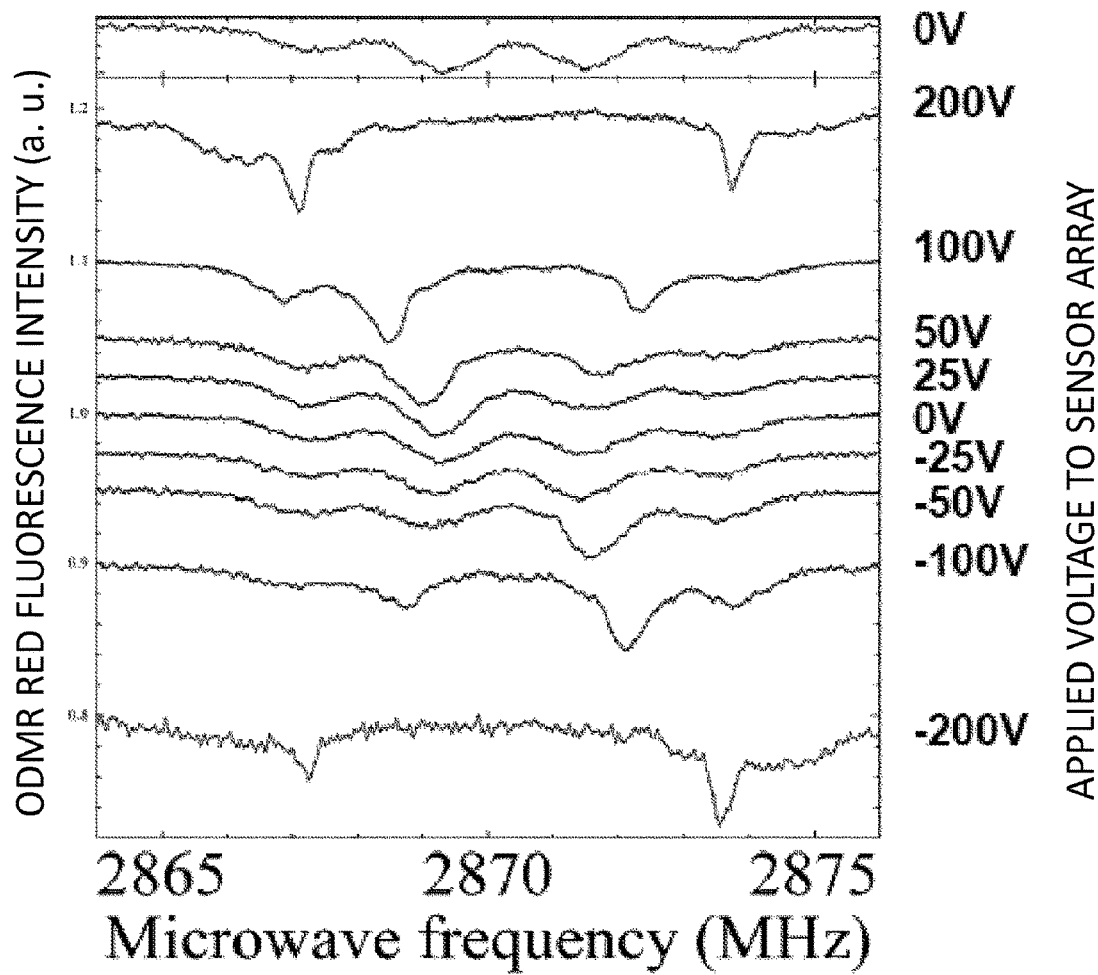
FIG. 18 is a view for describing that a line width of an ODMR signal becomes sharp when an electric field has been applied to the sensor array according to the present invention.

FIG. 18 is a view for describing that a line width of an ODMR signal becomes sharp when an electric field has been applied to the sensor array 20. In the example shown in the figure, the electric field has been applied to the sensor array 20 in a range of +200V to −200V, but in any of a positive electric field and a negative electric field, such a state can be clearly confirmed that as the applied voltage (absolute value thereof) increases, the line width of the ODMR signal becomes sharp.

This phenomenon is thought to have occurred because the distribution of the density of the electron spin in the NV center in the first region of the sensor array 20 varies according to the applied electric field, and as a result, a magnitude of an interaction between the electron spin and a nuclear spin varies. Such a reduction in the line width of the ODMR signal can remarkably enhance the sensitivity of the magnetic sensor. Incidentally, the diamond device according to the present invention is not limited to the application to the magnetic sensor and the magnetic measurement device, and can be applied also to various sensors such as a temperature sensor, an electric field sensor, current sensor and an acceleration sensor, and to a measurement device using the sensors.

The embodiments of the present invention have been described above with reference to the drawings. The aspects included in the present invention are summarized as follows, for example:

A diamond crystal according to a first aspect of the present invention has an NV region that contains a complex (NV center) of nitrogen (N) substituted with a carbon atom and a vacancy (V) located adjacent to the nitrogen, on a surface or in the vicinity of the surface, wherein the NV region has a donor concentration equal to or higher than a concentration of the NV centers.

The donor concentration in the NV region is preferably $1 \times 10^{12}$ cm$^{-3}$ or higher.

The donor is, for instance, phosphorus (P).

The face orientation of the NV region is preferably a {111} face, or a face having an off-angle that is ±10 degrees or less against the {111} face.

In addition, the above described NV region is preferably a diamond film that has been formed on a diamond substrate with a CVD method.

A diamond crystal of a second aspect according to the present invention has an NV region that contains a complex (NV center) of nitrogen (N) substituted with a carbon atom and a vacancy (V) located adjacent to the nitrogen, on a surface or in the vicinity of the surface, wherein a crystal face of the NV region is a {111} face or a face having an off-angle that is ±10 degrees or less against the {111} face, and a principal axis of the NV center is a <111> axis that is perpendicular to the {111} face.

The NV region has preferably a donor concentration equal to or higher than the concentration of the NV centers.

In addition, the donor concentration in the NV region is preferably $1 \times 10^{12}$ cm$^{-3}$ or higher.

The donor is, for instance, phosphorus (P).

IN addition, the above described NV region is preferably a diamond film that has been formed on a diamond substrate with a CVD method.

A diamond device of a first aspect according to the present invention includes a second region formed so as to be in contact with a first region that contains a complex (NV center) of nitrogen (N) substituted with a carbon atom of the diamond and a vacancy (V) located adjacent to the nitrogen, and has a donor concentration higher than that in the first region.

It is preferable that the first regions are two-dimensionally and periodically arrayed in a plane, and second regions each having a donor concentration higher than that in the first region are formed on respective side faces or peripheries of the first regions.

In addition, it is preferable that the second region is formed of n-type diamond, and the first region is formed of i-type or p-type diamond.

In addition, the second region has preferably an n$^+$ type of conductivity type of which the donor level is $1 \times 10^{18}$ cm$^{-3}$ or higher.

The donor is, for instance, phosphorus (P).

It is preferable that the face orientation of the first region is a {111} face or a face having an off-angle that is ±10 degrees or less against the {111} face, and a principal axis of the NV center is a <111> axis that is perpendicular to the {111} face.

In addition, the first region has preferably a donor concentration equal to or higher than the concentration of the NV centers in the first region.

In addition, each of the first regions is preferably surrounded by the second region in which the concentration of the NV centers is lower than that in the first region.

In addition, the above described diamond is preferably a diamond film that has been formed on a substrate with a CVD method.

Furthermore, each of the first regions has preferably an electrode for applying a positive potential provided on one principal surface side (rear face side), through an insulating film.

A diamond device of a second aspect according to the present invention includes an electrode for applying a positive potential, which is provided through an insulating film, on one principal surface side (rear face side) of the first region that contains the complex (NV center) of nitrogen (N) substituted with the carbon atom of the diamond and the vacancy (V) located adjacent to the nitrogen.

It is preferable that the first regions are two-dimensionally and periodically arrayed in a plane, and the electrodes for applying the positive potential are provided on the respective one principal surface sides (rear face sides) of the first regions, through an insulating film.

In addition, it is preferable that the face orientation of the first region is a {111} face or a face having an off-angle that is ±10 degrees or less against the {111} face, and a principal axis of the NV center is a <111> axis that is perpendicular to the {111} face.

In addition, the first region has preferably a donor concentration equal to or higher than the concentration of the NV centers in the first region.

The donor is, for instance, phosphorus (P).

Each of the first regions is preferably surrounded by the second region in which the concentration of the NV centers is lower than that in the first region.

In addition, the above described diamond is preferably a diamond film that has been formed on a substrate with a CVD method.

In the present invention, it is preferable that the diamond device further has an electric field generating unit that has at least two electrodes that are provided so as to face each other, on upper and lower face sides or side face sides of the diamond crystal portion containing the first region.

In addition, in the present invention, the periodic array of the first regions is, for instance, a square periodic array in which the center of the first region is positioned on each lattice point of a two-dimensional square lattice, when the plane is viewed from above.

Furthermore, in the present invention, the periodic array of the first regions is, for instance, a hexagonal packed array in which on six vertexes of a regular hexagon that has a center point on a center position of a particular first region, the centers of the other first regions are positioned respectively, when the plane is viewed from above.

A magnetic sensor according to the present invention includes: the above described diamond device; and an optical sensor that detects an optical signal that is an optical signal emitted from the respective surfaces of the first regions in the diamond device and is generated originating from electron spin resonance in the NV center.

In addition, a magnetic measurement device according to the present invention is a magnetic measurement device provided with the above described magnetic sensor, and includes: a sample stage that is provided so as to face the sensor array; an optical system that irradiates the diamond device with green light; a microwave generating unit that irradiates the diamond device with a microwave of which the frequency is variable; and a signal processing unit that processes an optical signal that has been detected by the optical sensor and has been generated originating from electron spin resonance in the NV center.

The magnetic measurement device according to the present invention preferably further has an electric field generating unit having at least two electrodes that are provided so as to face each other, on upper and lower face sides or side face sides of the diamond crystal portion containing the first region.

A method for manufacturing a sensor array of a first aspect according to the present invention includes: forming columnar portions that are two-dimensionally and periodically arrayed on the surface of a plate-like diamond, as first regions; forming a complex (NV center) of nitrogen (N) substituted with a carbon atom of the diamond and a vacancy (V) located adjacent to the nitrogen, in each of the first regions; and forming second regions that are second regions that surround respective peripheries of the first regions and each have a donor concentration higher than that in the first region.

A method for manufacturing a sensor array of a second aspect according to the present invention includes: forming columnar portions that are two-dimensionally and periodically arrayed on the surface of a plate-like diamond, as first regions; forming a complex (NV center) of nitrogen (N) substituted with a carbon atom of the diamond and a vacancy (V) located adjacent to the nitrogen, in each of the first regions; forming second regions that are second regions that surround respective peripheries of the first regions and each have a donor concentration higher than that in the first region; and providing an electrode for applying a positive potential on one principal surface side of the first region (rear face side), through an insulating film.

The second region is preferably formed so as to have an NV center concentration lower than that in the first region.

The periodic array of the first regions shall be, for instance, a square periodic array in which the center of the first region is positioned on each lattice point of a two-dimensional square lattice, when the plane is viewed from above.

In addition, the periodic array of the first regions shall be, for instance, a hexagonal packed array in which on six vertexes of a regular hexagon that has a center point on a center position of a particular first region, the centers of the other first regions are positioned respectively, when the plane is viewed from above.

The crystal face of the first region shall be preferably a {111} face or a face having an off-angle that is ±10 degrees or less against the {111} face.

In addition, the second region shall be preferably formed of n-type diamond, and the first region shall be preferably formed of i-type or p-type diamond.

In addition, the second region shall be preferably $n^+$ type diamond of which the donor level is $1 \times 10^{18}$ cm$^{-3}$ or higher.

In addition, the donor concentration in the first region is preferably controlled to be equal to or higher than the concentration of the NV centers in the first region.

Furthermore, the above described diamond is preferably formed as a diamond film that is formed on a substrate with a CVD method.

The method for manufacturing the sensor array of another aspect according to the present invention includes forming a plurality of junctions of a heterogeneous conductivity type that is formed of diamond and has a complex (NV center) of nitrogen (N) substituted with a carbon atom of the diamond and a vacancy (V) located adjacent to the nitrogen, formed in the region of the junction, on a principal surface of a plate-like diamond. Incidentally, the aspect may be such an aspect of having means for injecting current into the junctions of the heterogeneous conductivity type or means for applying a voltage thereto.

INDUSTRIAL APPLICABILITY

The diamond crystal according to the present invention enables almost 100% of the complex (NV center) of the nitrogen (N) substituted with the carbon atom and the vacancy (V) located adjacent to the nitrogen to be in a negatively charged state (NV$^-$), and also enables spin states of the NV$^-$ centers to be aligned in one direction; and a peak of an optically detected magnetic resonance (ODMR: Optically Detected Magnetic Resonance) signal becomes sharp, and besides, a contrast is also enhanced.

Furthermore, the diamond device according to the present invention can keep the NV center formed in the above described diamond crystal in a negatively charged state (NV$^-$).

As a result, the magnetic sensor that is provided with the diamond device according to the present invention enables two-dimensional magnetic measurement at ordinary temperature in the atmosphere to be carried out with high sensitivity as compared with a conventional one.

Incidentally, the above described effect can be obtained not only in the diamond device and the like that use a complex (NV center) of nitrogen (N) substituted with a carbon atom of the diamond and a vacancy (V) located adjacent to the nitrogen, but a similar effect can be obtained also in a diamond device and the like that use a complex of an device such as Si, P and Ge that substitute for the carbon atom of the diamond and a vacancy (V) located adjacent to the substituting device. Incidentally, the diamond device according to the present invention is not limited to the application to the magnetic sensor and the magnetic measurement device, but can be applied also to various sensors such as a temperature sensor, an electric field sensor, current sensor and an acceleration sensor, and to a measurement device using the sensors.

REFERENCE SIGNS LIST 10 and 10a diamond substrate
10b diamond thin film
11 first region (columnar portion)
12 first mask
13 second mask
14a and 14b third mask
15 second region
16 pillar
17 p⁻ type or i-type diamond thin film
17a columnar portion
18 mask
19 n-type diamond film
20 sensor array
21 optical sensor
22 sample stage
23 specimen
24 optical system
24a light source
24b irradiation lens
24c dichroic mirror
25 microwave generating unit
26 signal processing unit
27 module
28 control circuit
29 electric field generating unit
100 magnetic measurement system

The invention claimed is:

1. A diamond device using diamond, comprising a second region formed so as to be in contact with a first region that contains a complex (NV center) of nitrogen (N) substituted with a carbon atom of the diamond and a vacancy (V) located adjacent to the nitrogen, and has a donor concentration higher than that in the first region, wherein
the diamond is a n-type diamond film that is formed on a substrate by a CVD method,
the first regions are two-dimensionally and periodically arrayed in a plane, and the second regions each having the donor concentration higher than that in the first region are formed on respective side faces or peripheries of the first regions, and
a crystal face of the first region is a {111} face or a face having an off-angle that is ±10 degrees or less against the {111} face, and a principal axis of the NV center is a <111> axis that is perpendicular to the {111} face.

2. The diamond device according to claim 1, wherein the second region is formed of n-type diamond, and the first region is formed of i-type or p-type diamond.

3. The diamond device according to claim 1, wherein the second region is formed of n-type diamond, and the first region is a depletion region formed by a p-n junction.

4. The diamond device according to claim 1, wherein the second region has an n+ type of conductivity type of which a donor level is $1 \times 10^{18}$ cm$^{-3}$ or higher.

5. The diamond device according to claim 1, wherein a second region that has an NV center concentration lower than that in the first region is formed so as to be in contact with the first region.

6. The diamond device according to claim 1, wherein the first region has a donor concentration equal to or higher than the concentration of the NV centers in the first region.

7. The diamond device according to claim 1, wherein the donor concentration is in a range of $10 \times 10^{15}$ cm$^{-3}$ to $10 \times 10^{19}$ cm$^{-3}$.

8. The diamond device according to claim 1, further comprising an electric field generating unit that has at least two electrodes that are provided so as to face each other, on upper and lower face sides or side face sides of a diamond crystal portion containing the first region.

9. The diamond device according to claim 1, wherein a periodic array of the first regions is a square periodic array in which the center of the first region is positioned on each lattice point of a two-dimensional square lattice, when the plane is viewed from above.

10. The diamond device according to claim 1, wherein a periodic array of the first regions is a hexagonal packed array in which on six vertexes of a regular hexagon that has a center point on a center position of a particular first region, the centers of the other first regions are positioned respectively, when the plane is viewed from above.

11. A magnetic sensor comprising:
the diamond device according to claim 1; and
an optical sensor that detects an optical signal that is an optical signal emitted from the respective surfaces of the first regions and is generated originating from electron spin resonance in the NV center.

12. A magnetic measurement system provided with the magnetic sensor according to claim 11, comprising:
a sample stage that is provided so as to face the diamond device; an optical system that irradiates the diamond device with green light;
a microwave generating unit that irradiates the diamond device with a microwave of which a frequency is variable; and
a signal processing unit that processes an optical signal that has been detected by the optical sensor and has been generated originating from electron spin resonance in the NV center.

13. The magnetic measurement system according to claim 12, further comprising: an electric field generating unit that has at least two electrodes that are provided so as to face each other, on upper and lower face sides or side face sides of a diamond crystal portion containing the first region.

14. The diamond device according to claim 1, further comprising an electrode for applying a positive potential, which is provided through an insulating film, on one principal surface side of the first region.

15. The diamond device according to claim 1, wherein the first regions are two-dimensionally and periodically arrayed in a plane, and electrodes for applying a positive potential are provided on respective one principal surface sides of the first region, through an insulating film.

* * * * *